US012192682B2

(12) United States Patent
Abbas

(10) Patent No.: US 12,192,682 B2
(45) Date of Patent: *Jan. 7, 2025

(54) PATIENT ROOM REAL-TIME MONITORING AND ALERT SYSTEM

(71) Applicant: Vitalchat, Inc., Ashburn, VA (US)

(72) Inventor: Ghafran Abbas, Ashburn, VA (US)

(73) Assignee: Vitalchat, Inc., Ashburn, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/444,921

(22) Filed: Feb. 19, 2024

(65) Prior Publication Data

US 2024/0236277 A1 Jul. 11, 2024

Related U.S. Application Data

(63) Continuation of application No. 18/299,876, filed on Apr. 13, 2023, now Pat. No. 11,943,567, which is a continuation of application No. 17/321,903, filed on May 17, 2021, now Pat. No. 11,671,566, which is a continuation-in-part of application No. 17/110,468, filed on Dec. 3, 2020, now Pat. No. 11,076,778.

(60) Provisional application No. 63/170,611, filed on Apr. 5, 2021.

(51) Int. Cl.
*H04N 7/18* (2006.01)
*G06F 18/2431* (2023.01)
*G06V 20/52* (2022.01)
*G06V 40/20* (2022.01)
*G08B 5/22* (2006.01)

(52) U.S. Cl.
CPC ......... *H04N 7/183* (2013.01); *G06F 18/2431* (2023.01); *G06V 20/52* (2022.01); *G06V 40/23* (2022.01); *G08B 5/22* (2013.01)

(58) Field of Classification Search
CPC .... H04N 7/183; G06F 18/2431; G06V 20/52; G06V 40/23; G08B 5/22
See application file for complete search history.

(56) References Cited

U.S. PATENT DOCUMENTS

| | | |
|---|---|---|
| 2010/0049095 A1 | 2/2010 | Bunn et al. |
| 2012/0075464 A1 | 3/2012 | Derenne et al. |
| 2013/0015980 A1 | 1/2013 | Evans et al. |
| 2015/0112151 A1 | 4/2015 | Muhsin et al. |
| 2015/0300872 A1 | 10/2015 | Hirose et al. |
| 2017/0155877 A1 | 6/2017 | Johnson et al. |
| 2019/0205630 A1 | 7/2019 | Kusens |
| 2020/0242471 A1 | 7/2020 | Busch |

*Primary Examiner* — Nabil H Syed
*Assistant Examiner* — Cal J Eustaquio
(74) *Attorney, Agent, or Firm* — Young Basile Hanlon & MacFarlane, P.C.

(57) ABSTRACT

A monitoring device obtains an image stream of at least a part of a room of a patient. The monitoring device identifies, from a first image of the image stream, first states of the part of the room. The monitoring device identifies, from a second image of the image stream, second states of the part of the room. The monitoring device compares the first states to the second states to identify a change indicating an active state. The monitoring device transmits, in response to identifying the active state, a notification to a server. The server transmits, in response to receiving the notification, an alert to a user device associated with a healthcare provider.

20 Claims, 11 Drawing Sheets

PATIENT ROOM REAL-TIME MONITORING AND ALERT SYSTEM

CROSS-REFERENCE TO RELATED APPLICATION(S)

This application is a continuation of U.S. patent application Ser. No. 18/299,876, filed Apr. 13, 2023, which is a continuation of U.S. patent application Ser. No. 17/321,903, filed May 17, 2021, which is a continuation-in-part of U.S. patent application Ser. No. 17/110,468, filed Dec. 3, 2020, which claims priority to and the benefit of U.S. Provisional Patent Application No. 63/170,611, filed Apr. 5, 2021, the entire disclosures of which are incorporated herein by reference.

TECHNICAL FIELD

This disclosure relates generally to patient state detection using machine learning.

BACKGROUND

The use for telehealth, telemonitoring, and/or televisits has been increasing and the need for such capabilities has increased especially in response to the COVID-19 pandemic. "Tele" in this context means "from a distance" or "remotely," and more specifically using telecommunication capabilities. Patient rooms may be equipped (in a fixed or in a movable way) with a telecommunication device (i.e., a monitoring device) that enables telehealth, telemonitoring, televisits, and/or the monitoring of different aspects of a patient and/or a patient's room. The monitoring device may enable audio and/or visual communication between a remote user (e.g., a physician, a family member, etc.) and an in-room person (e.g., the patient, a nurse, etc.).

SUMMARY

A first aspect of the disclosed implementations is A method that includes obtaining, by a monitoring device, an image stream of at least a part of a room of a patient; identifying, by the monitoring device from a first image of the image stream, first states of the part of the room; identifying, by the monitoring device from a second image of the image stream, second states of the part of the room; comparing, by the monitoring device, the first states to the second states to identify a change indicating an active state; transmitting, by the monitoring device in response to identifying the active state, a notification to a server; and transmitting, by the server in response to receiving the notification, an alert to a user device associated with a healthcare provider.

A second aspect of the disclosed implementations is a system that includes monitoring device, a server, and a user device associated with a healthcare provider. The monitoring device is configured to obtain an image stream of at least a part of a room of a patient; identify first states of the part of the room from a first image of the image stream; identify second states of the part of the room from a second image of the image stream; compare the first states to the second states to identify a change indicating an active state; and transmit a notification to the server in response to identifying the active state. The server is configured to receive the notification from the monitoring device and transmit an alert in response to the notification to a user device. The user device is configured to receive the alert from the server.

A third aspect of the disclosed implementations are non-transitory computer-readable media having stored thereon instructions that, when executed by one or more processors, cause the one or more processors to perform operations that include obtaining, by a monitoring device, an image stream of at least a part of a room of a patient; identifying, by the monitoring device from a first image of the image stream, first states of the part of the room; identifying, by the monitoring device from a second image of the image stream, second states of the part of the room; comparing, by the monitoring device, the first states to the second states to identify a change indicating an active state; transmitting, by the monitoring device in response to identifying the active state, a notification to a server; and transmitting, by the server in response to receiving the notification, an alert to a user device associated with a healthcare provider.

These and other aspects of the present disclosure are disclosed in the following detailed description of the embodiments, the appended claims, and the accompanying figures.

It will be appreciated that aspects can be implemented in any convenient form. For example, aspects may be implemented by appropriate computer programs which may be carried on appropriate carrier media which may be tangible carrier media (e.g., disks) or intangible carrier media (e.g., communications signals). Aspects may also be implemented using suitable apparatus which may take the form of programmable computers running computer programs arranged to implement the methods and/or techniques disclosed herein. Aspects can be combined such that features described in the context of one aspect may be implemented in another aspect.

BRIEF DESCRIPTION OF THE DRAWINGS

The disclosure is best understood from the following detailed description when read in conjunction with the accompanying drawings.

Figure 1:
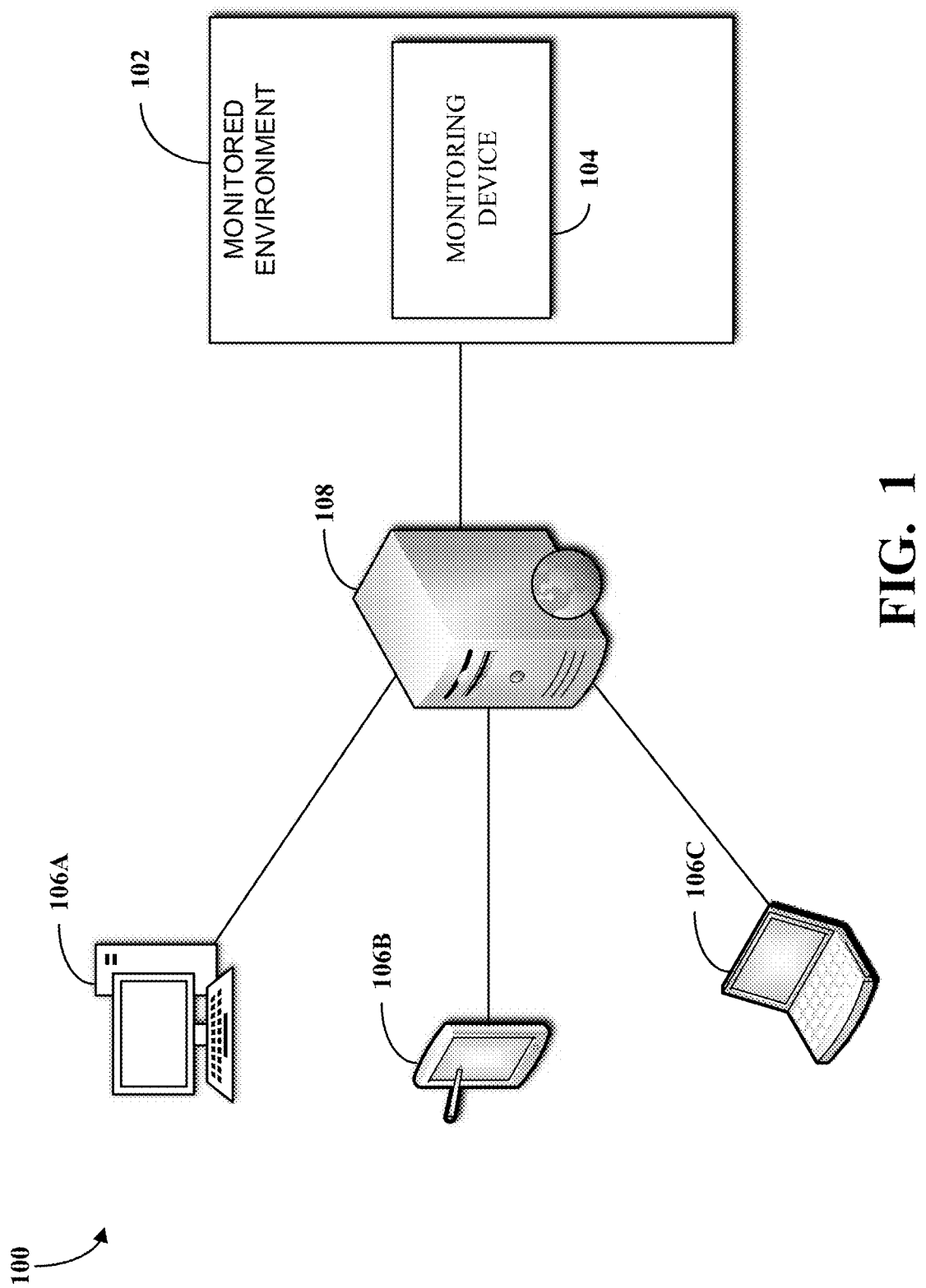
FIG. 1 is an schematic of an example of a system according to implementations of this disclosure.

These and other aspects of the present disclosure are disclosed in the following detailed description of the embodiments, the appended claims, and the accompanying figures.

It will be appreciated that aspects can be implemented in any convenient form. For example, aspects may be implemented by appropriate computer programs which may be carried on appropriate carrier media which may be tangible carrier media (e.g., disks) or intangible carrier media (e.g., communications signals). Aspects may also be implemented using a suitable apparatus, which may take the form of programmable computers running computer programs arranged to implement the methods and/or techniques disclosed herein. Aspects can be combined such that features described in the context of one aspect may be implemented in another aspect.

DETAILED DESCRIPTION

It is critical that a patient and/or the patient's room be monitored for adverse conditions that may negatively impact the patient. For example, a lowered bed rail of the patient's bed presents the risk that the patient may fall off the bed. For example, if the patient remains lying one the same side of his/her body for over a certain period of time (e.g., more than two hours) without being repositioned, then bedsores (also known as pressure ulcers) may develop. Bedsores are a common, painful, debilitating, and potentially deadly condition. For example, if the patient gets out of his/her bed, such as to use the restroom, but does not return within a reasonable period of time, then there is a risk that the patient may have fallen and/or is unable to return to the bed. For example, a steep bed incline presents the risk that the patient's breathing may be obstructed.

Proper patient care can include fall prevention, bed sore prevention, bed incline monitoring for breathing monitoring, and/or the detection or prevention of other adverse conditions (e.g., monitored conditions). When an adverse condition and/or the potential for an adverse condition is detected, a care provider (e.g., a nurse, etc.) can be notified so that the care provider can take appropriate corrective and/or preventative measures. To illustrate, and without loss of generality, if a patient has been lying on his/her back for more than two hours, then a notification (e.g., an alert, a message, etc.) may be sent a nurse so that the nurse can reposition the patient. The alert can be sent in one or more ways to a user device. For example, a text message may be sent to a hand-held device of the nurse. For example, the alert may be displayed on a display at a nurses station. Other ways of alerting care providers are possible.

Detection of (potential) adverse conditions according to implementations of this disclosure actively monitor bed states and/or states of other aspects of a patient's room (collectively, room state or, simply, state). An in-room monitoring device, which includes a camera, can be used to actively monitor the room state. Image processing can be used to detect (e.g., infer, calculate, obtain, output, etc.) the room state. For example, a machine learning (ML) model can be trained to detect the room state. In an example, the ML model can be a multi-label image classification model.

Implementations according to this disclosure can detect a state (e.g., a room state) of a monitored environment (e.g., a hospital room) and/or a part thereof (e.g., a hospital bed, a patient, etc.). The room state can be detected without any special hardware sensors. A monitoring device that includes a camera can be used to monitor the monitored environment and determine the states using machine learning and computer vision. Traditionally, and with respect to detecting different states of a hospital bed, existing beds may be retrofitted with specialized hardware sensors or new beds (which may be referred to as smart beds) that already include such sensors may be used. However, these can be costly prepositions for hospitals. Another traditional approach for monitoring a room is to rely in a human who would regularly visually inspect a patient's room to determine the room state. However, this approach is not efficient, is prone to mistakes, and is expensive.

Traditionally, a human may be tasked with monitoring several monitored environments simultaneously. For example, a nurse may be tasked with monitoring the rooms of 15, 20, or more patients simultaneously. Video feeds from each of the monitored environments may be displayed on a user device (e.g., a monitoring station, a nurses station, etc.) of the human. The human has to attempt to watch for adverse, or potentially adverse, states (e.g., conditions, occurrences, etc.) in all of the monitored environments at the same time by simultaneously monitoring all the video feeds.

Such traditional approaches can present several problems. The user device must have sufficient computational resources to receive, process (e.g., decode, etc.), and display several video streams simultaneously. The computing infrastructure (e.g., network) must have sufficient bandwidth to support the video streams. The possibility of degraded performance and increased usage of compute and/or network resources may also include increased investment in processing, memory, and storage resources for the user device and network, which result in increased energy expenditures (needed to operate those increased processing, memory, and storage resources, or for the network transmission of the intermediate data) and associated emissions that may result from the generation of that energy. Furthermore, and more importantly, the human may suffer from information overload causing the human to overlook or miss critical states in the monitored environments.

Implementations according to this disclosure can focus the attention of a human who may be monitoring multiple monitored environments. The attention of the human can be focused on (e.g., directed to, etc.) those monitored environments currently exhibiting certain active states. The monitoring device can monitor for (e.g., detect, infer, etc.) several states in/of the monitored environment. A state that is detected is referred to herein an active state. An active state is a state that has a certain value. If the state has another value, then it may not be considered active. A state, as used herein, can refer to a condition of interest of the monitored environment. The state can have one or more values. The states of interest can include conditions, events, occurrences, and the like of the monitored environment.

A state of interest that is detected is referred to herein as an active state. A state of interest that is not detected is referred to herein as an inactive state. For example, a state of interest may be whether the patient is waving. If the patient is determined to be waving, then the patient-waving state may have a value of "yes," "1," "true," "waving" or any other value indicating that the patient is waving; if the patient is not waving, then the patient-waving state may have a value of "no," "0," "false," "not waving" or any other value indicating that the patient is not waving. Furthermore, if the human is to be notified of a state when the state (e.g., the patient-waving state) has a certain value (e.g., "yes"), then if the state is detected to have that certain value, the state is referred to herein as an active state.

A detected state that persists for a predetermined duration is referred to herein as a persistent state or as a state that persists for the predetermined duration.

Monitored environments can be monitored by respective monitoring devices. The monitoring devices can be communicatively connected to a server that can in turn be communicatively connected to a user device. A monitoring device that is monitoring a monitored environment can obtain images (e.g., an image stream or a video stream) from a camera. Images of the monitored environment can be continuously captured using the camera. The monitoring device can apply a machine learning model to at least some of the images to determine respective states of the monitored environment. The monitoring device can record the states. Responsive to detecting a state change (e.g., a state becoming active or persistent) from one image to a next image, the monitoring device can transmit a notification to a central server. The notification can include a snapshot of the monitored environment. The notification can include a list of the detected active states and the persistent states.

Attention focusing for multiple monitored environments can minimize information overload, direct the focus (e.g., attention) of the human to a subset of the monitored environments, and require fewer compute and network resources than traditional approaches. In an implementation, and as further described herein, implementations according to this disclosure enable humans (e.g., heath care professionals) to accurately provide proper attention to the patients that need it. Attention focusing for multiple monitored environments also reduces the need for live (e.g., streaming, etc.) feeds of the monitored environments.

Details of room state detection via camera and attention focusing for multiple patients monitoring are described herein with initial reference to a system in which the teachings herein can be implemented.

FIG. 1 is a schematic of an example of a system 100 according to implementations of this disclosure. The system 100 includes a monitored environment 102, a monitoring device 104, a user device 106, and a server 108.

The monitored environment 102 can be a patient hospital room, a nursing home room, a room of a home patient, a manufacturing line, a workstation, a laboratory, and the like. The monitored environment 102 includes and/or can be viewed using the monitoring device 104. The monitored environment 102 can be remotely monitored from the user device 106. The user device 106 can be one or more of a desktop computer 106A, a mobile device 106B (such as tablet, a smart phone, and the like), a laptop computer 106C, or some other device that can be used to access, communicate with, and/or control (directly or indirectly) the monitoring device 104. A user (not shown) of the user device 106 can monitor the monitored environment 102 via the monitoring device 104. That the monitored environment 102 is remotely monitored by the user means that the user may not physically be in the monitored environment 102 while performing the monitoring.

In the case that the monitored environment 102 is a patient hospital room, the user can be a physician, a nurse, another health-care practitioner, a family member of the patient, and/or the like. For example, the physician may be remotely responding to (e.g., diagnosing, mitigating, assessing, etc.) a patient emergency or remotely performing patient rounds. The nurse may be monitoring patients, including the monitored environment 102 from a nurses station to, for example, ensure that no patient is falling, is in need of help, is distressed, and/or the like. The family member of the patient may remotely visit with the patient using the monitoring device 104.

The monitoring device 104 can be configured to and/or used to capture video, images, audio, environmental conditions, or other characteristics of the monitored environment. The characteristics of the monitored environment can be transmitted to one or more users of the user devices 106. Via the user device 106, the user can interact with the monitoring device, such as by sending and/or receiving captured video and/or audio, sending commands to the monitoring device 104, and the like.

The user device 106 and the monitoring device 104 can communicate via the server 108. For example, the user device 106 can send commands to the server 108, which relays the command to the monitoring device. Similarly, the monitoring device 104 can send information to the server 108, which relays the information to the user device 106.

To illustrate, the monitoring device 104 can include a camera that is configured to view the monitored environment 102. The user device 106 can issue a request to the server 108 to establish a connection with the monitoring device 104. The server 108 can establish the connection. Issuing a request to the server 108 to establish a connection can include, for example, the user device 106 connecting to a patient by the patient's room number or name; the server 108 determining the monitoring device 104 of the patient (i.e., the monitoring device that is in the patient's room); and the server 108 connecting the user device 106 and the monitoring device 104. The connection session may be an video communication session during which the user can communicate visually and/or verbally with a person in the patient's room. The user device 106, may during the connection session, send a pan, tilt, or zoom (PTZ) command to the camera of the monitoring device 104 via the server 108. The monitoring device 104 can update the view of the monitored environment according to the PTZ command and send back, via the server 108, a video and/or image of the updated view of the monitored environment, which can then be displayed on a display of the user device 106. In an example, the server 108 can allow certain users to control monitoring device and not allowing other user devices to control the monitoring device.

In another example (not shown), the user device 106 can establish a peer-to-peer communication channel with the monitoring device 104. For example, in response to the connection request, the server 108 can facilitate the establishment of the peer-to-peer (e.g., direct) communication between the user device 106 and the monitoring device 104.

The server 108 can be deployed (e.g., physically located) on premise at the location of the monitored environment. The server 108 can be deployed on a same local area network (LAN) of the monitoring device 104. The server 108 can be deployed on a same wide area network (WAN) of the monitoring device 104. The server 108 can be a cloud-based server. Other deployments of the server 108 are possible.

The monitoring device 104, the user device 106, and the server 108 can communicate over any suitable network. The network (not shown) can be, for example, the Internet or an Internet Protocol (IP) network, such as the World Wide Web. The network can be a LAN, a WAN, a virtual private network (VPN), cellular telephone network, a private network, an extranet, an intranet, any other means of transferring information (e.g., video streams, audio streams, images, other information), or a combination thereof from one end point to another end point.

In an example, the user device 106 and the monitoring device 104 may communicate using a real-time transport protocol (RTP) for transmission of the media content, which may be encoded, over the network. In another implementation, a transport protocol other than RTP may be used (e.g., a Hypertext Transfer Protocol-based (HTTP-based) streaming protocol). For example, the user device 106 can transmit and/or receive media content (e.g., audio and/or video content) to and/or from the monitoring device 104 via WebRTC, which provides web browsers and mobile applications with real-time communication. However, the disclosure herein is not so limited and any other real-time transmission protocol can be used.

Figure 2:
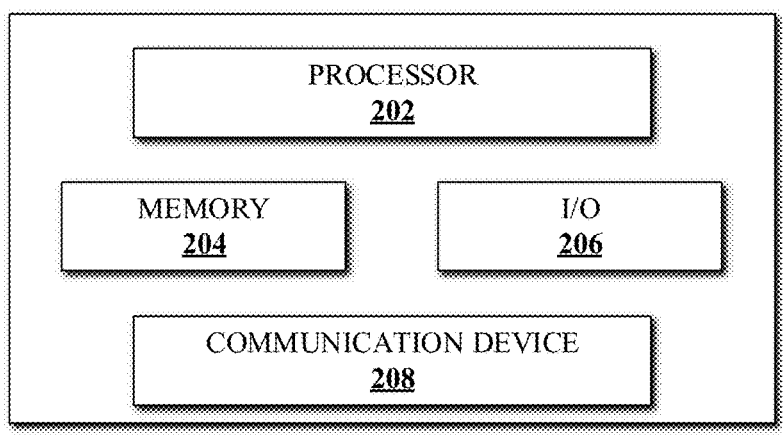
FIG. 2 is a block diagram of an example of a computing device.

FIG. 2 is a block diagram of an example of a computing device 200. Each of the monitoring device 104, the user device 106, or the server 108 can be implemented, at least partially, by the computing device 200.

The computing device 200 can be implemented by any configuration of one or more computers, such as a microcomputer, a mainframe computer, a supercomputer, a general-purpose computer, a special-purpose/dedicated computer, an integrated computer, a database computer, a remote server computer, a personal computer, a laptop computer, a tablet computer, a cell phone, a personal data assistant (PDA), a wearable computing device, or a computing service provided by a computing service provider, for example, a web host or a cloud service provider. In some implementations, the computing device can be implemented in the form of multiple groups of computers that are at different geographic locations and can communicate with one another, such as by way of a network. While certain operations can be shared by multiple computers, in some implementations, different computers are assigned to different operations. In some implementations, the system 100 can be implemented using general-purpose computers/processors with a computer program that, when executed, carries out any of the respective methods, algorithms, and/or instructions described herein. In addition, or alternatively, for example, special-purpose computers/processors including specialized hardware can be utilized for carrying out any of the methods, algorithms, or instructions described herein.

The computing device 200 can have an internal configuration of hardware including a processor 202 and a memory 204. The processor 202 can be any type of device or devices capable of manipulating or processing information. In some implementations, the processor 202 can include a central processor (e.g., a central processing unit or CPU). In some implementations, the processor 202 can include a graphics processor (e.g., a graphics processing unit or GPU). Although the examples herein can be practiced with a single processor as shown, advantages in speed and efficiency can be achieved by using more than one processor. For example, the processor 202 can be distributed across multiple machines or devices (each machine or device having one or more processors) that can be coupled directly or connected via a network (e.g., a local area network). The memory 204 can include any transitory or non-transitory device or devices capable of storing executable codes and data that can be accessed by the processor (e.g., via a bus). The memory 204 herein can be a random-access memory (RAM) device, a read-only memory (ROM) device, an optical/magnetic disc, a hard drive, a solid-state drive, a flash drive, a security digital (SD) card, a memory stick, a compact flash (CF) card, or any combination of any suitable type of storage device. In some implementations, the memory 204 can be distributed across multiple machines or devices, such as in the case of a network-based memory or cloud-based memory. The memory 204 can include data (not shown), an operating system (not shown), and an application (not shown). The data can include any data for processing (e.g., an audio stream, a video stream, a multimedia stream, user commands, and/or other data). The application can include programs that permit the processor 202 to implement instructions to generate control signals for performing functions of the techniques in the following description.

In some implementations, in addition to the processor 202 and the memory 204, the computing device 200 can also include a secondary (e.g., external) storage device (not shown).

When present, the secondary storage device can provide additional memory when high processing needs exist. The secondary storage device can be a storage device in the form of any suitable non-transitory computer-readable medium, such as a memory card, a hard disk drive, a solid-state drive, a flash drive, or an optical drive. Further, the secondary storage device can be a component of the computing device 200 or can be a shared device accessible via a network. In some implementations, the application in the memory 204 can be stored in whole or in part in the secondary storage device and loaded into the memory 204 as needed for processing.

In addition to the processor 202 and the memory 204, the computing device 200 can include input/output (I/O) devices. For example, the computing device 200 can include an I/O device 206. The I/O device 206 can be implemented in various ways, for example, it can be a display that can be coupled to the computing device 200 and configured to display a rendering of graphics data. The I/O device 206 can be any device capable of transmitting a visual, acoustic, or tactile signal to a user, such as a display, a touch-sensitive device (e.g., a touchscreen), a speaker, an earphone, a light-emitting diode (LED) indicator, or a vibration motor. The I/O device 206 can also be any type of input device either requiring or not requiring user intervention, such as a keyboard, a numerical keypad, a mouse, a trackball, a microphone, a touch-sensitive device (e.g., a touchscreen), a sensor, or a gesture-sensitive input device. If the I/O device 206 is a display, for example, it can be a liquid crystal display (LCD), a cathode-ray tube (CRT), or any other output device capable of providing a visual output to an individual. In some cases, an output device can also function as an input device. For example, the output device can be a touchscreen display configured to receive touch-based input.

The I/O device 206 can alternatively or additionally be formed of a communication device for transmitting signals and/or data. For example, the I/O device 206 can include a wired means for transmitting signals or data from the computing device 200 to another device. For another example, the I/O device 206 can include a wireless transmitter or receiver using a protocol compatible to transmit signals from the computing device 200 to another device or to receive signals from another device to the computing device 200.

In addition to the processor 202 and the memory 204, the computing device 200 can optionally include a communication device 208 to communicate with another device. Optionally, the communication can be via a network. The network can be one or more communications networks of any suitable type in any combination, including, but not limited to, networks using Bluetooth communications, infrared communications, near-field communications (NFCs), wireless networks, wired networks, local area networks (LANs), wide area networks (WANs), virtual private networks (VPNs), cellular data networks, or the Internet. The communication device 208 can be implemented in various ways, such as a transponder/transceiver device, a modem, a router, a gateway, a circuit, a chip, a wired network adapter, a wireless network adapter, a Bluetooth adapter, an infrared adapter, an NFC adapter, a cellular network chip, or any suitable type of device in any combination that is coupled to the computing device 200 to provide functions of communication with the network.

The computing device 200 can also include or be in communication with an image-sensing device (not shown), for example a camera, or any other image-sensing device now existing or hereafter developed that can sense an image such as the image of a user operating the computing device 200 or a view of a monitored environment. The image-sensing device can be positioned such that it is directed to capture a view of the monitored environment. For example, the image-sensing device can be directed toward a patient and/or a patient bed in a hospital room. In an example, the position and optical axis of the image-sensing device can be configured and/or controlled such that the field of vision (i.e., the view) includes an area of interest.

The computing device 200 can also include or be in communication with a sound-sensing device, for example a microphone, or any other sound-sensing device now existing or hereafter developed that can sense sounds near the computing device 200. The sound-sensing device can be positioned or controlled to be positioned such that it is directed toward a monitored environment so as to capture speech, other utterances, or other sounds within the monitored environment. The sound-sensing device can be configured to receive sounds, for example, speech or other utterances made by the user while the user operates the computing device 200. The computing device 200 can also include or be in communication with a sound playing device.

The computing device 200 (and any algorithms, methods, instructions, etc., stored thereon and/or executed thereby) can be realized in hardware including, for example, intellectual property (IP) cores, application-specific integrated circuits (ASICs), programmable logic arrays, optical processors, programmable logic controllers, microcode, firmware, microcontrollers, servers, microprocessors, digital signal processors, or any other suitable circuit. In this disclosure, the term "processor" should be understood as encompassing any the foregoing, either singly or in combination. The terms "signal," "data," and "information" are used interchangeably.

Figure 3:
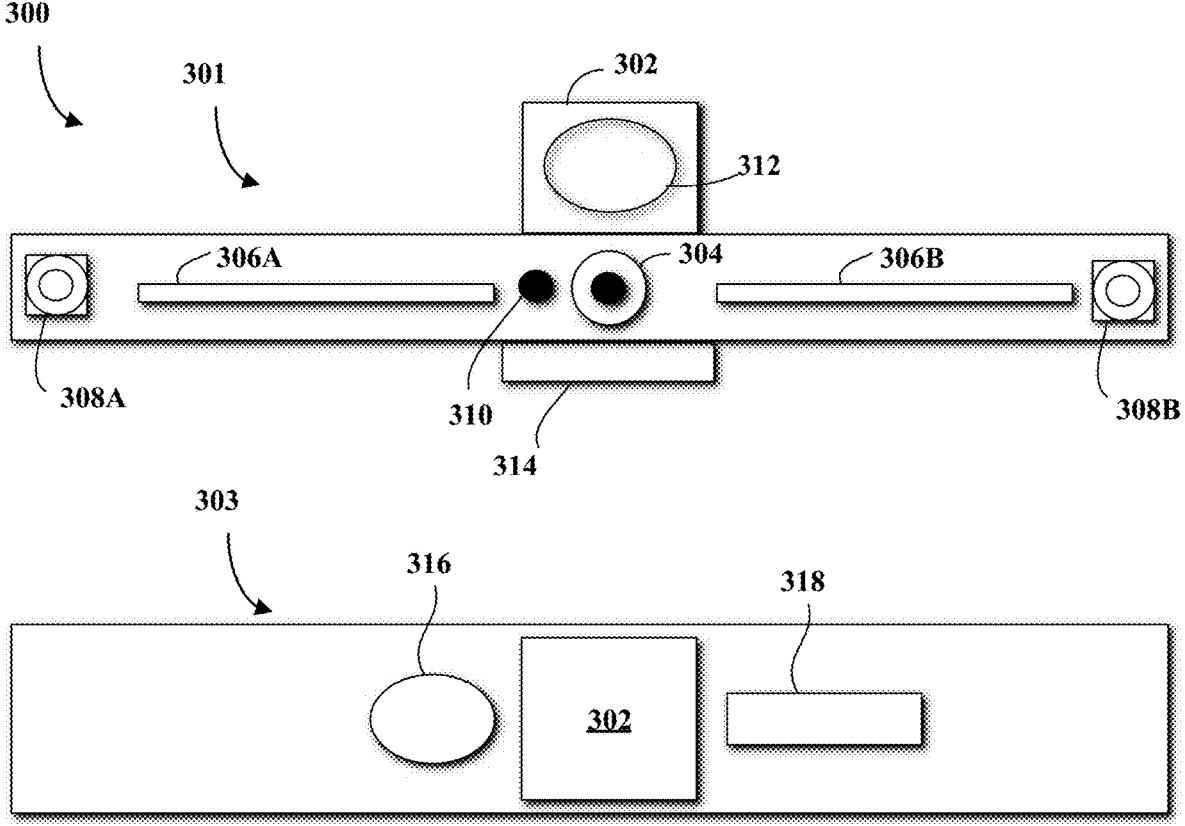
FIG. 3 is a block diagram of an example of a monitoring device according to implementations of this disclosure.

FIG. 3 is a block diagram of an example of a monitoring device 300 according to implementations of this disclosure. The monitoring device 300 can be the monitoring device 104 of FIG. 1. FIG. 3 shows a front view 301 and a top view 303 of the monitoring device 300. The front view 301 faces the monitored environment. The monitoring device 300 includes a camera 302, a fish-eye camera 304, microphone arrays 306A, 306B, infra-red light sensors 308A, 308B, a light sensor 310, a multi-color LED strip 312, a mounting device (i.e., a mount 314), a speaker 316, and a control panel 318. However, a monitoring device according to this disclosure is not so limited and can include fewer, additional, other sensors and/or components, or a combination thereof. While not specifically shown, the monitoring device 300 can also include a processor, as described with respect to the processor 202 of FIG. 2. The monitoring device 300 can also include a memory, such as the memory 204 if FIG. 2.

The camera 302 can be used to view the monitored environment. The camera 302 can include pan, tilt, zoom capabilities so that a remote user, via a user device, such as the user device 106 of FIG. 1, can control the camera 302 to pan, tilt, and/or zoom (PTZ) in order to adjust the view of the monitored environment to a desired view. That is, the monitoring device 300 can receive PTZ commands from the user device. The camera 302 can be capable of a magnification zoom factor of 10×, 12×, 20×, or some other magnification zoom factor. The fish-eye camera 304 can provide a 180° view of the monitored environment.

The microphone arrays 306A, 306B can be used to capture sounds in the monitored environment. The infra-red light sensors 308A, 308B can be used to improve viewing of the monitored environment, such as the monitoring device 104, under low light conditions, such as at night.

The light sensor 310 can be used to sense the ambient light present in the monitored environment. In an example, the amount of detected ambient light can be used to adjust an intensity of a display that may connected to the monitoring device 300. The multi-color LED strip 312 can be used to give a visual indication to an occupant of the monitored environment of an incoming video and/or audio call, that a video and/or audio call is ongoing, or that a video and/or audio call is not active. The multi-color LED strip 312 can be used to provide other visual indicators to the occupant of the monitored environment.

The mount 314 can be used to mount the monitoring device on top of a monitor or a television. In an example, the monitor can be a portable computing device, such as a tablet. In an example, the monitoring device 300 may not itself include a processor. However, via an external connection (shot shown), such as a USB connection, a firewire connection, a Bluetooth connection, or the like, can be connected to a general purpose computer to enable the general purpose computer to perform monitoring functions of the monitored environment. As such, by connecting the monitoring device 300 to any processing unit, the processing unit can be turned into a telehealth end point. In such a configuration, the monitoring device encompasses the processor-less monitoring device plus the processor to which the processor-less monitoring device is connected to.

The speaker 316 can be used to output sounds (e.g., voice, speech, etc.), such as those received from a user device, such as the user device 106 of FIG. 1. The control panel 318 can include controls for muting, unmuting, and controlling the volume of the speaker 316. The control panel 318 can also include controls for controlling whether the camera 302 is enabled or disabled. When the camera 302 is disabled, the camera 302 does not visually (via video or images) capture (e.g., view) the monitored environment.

Figure 4:
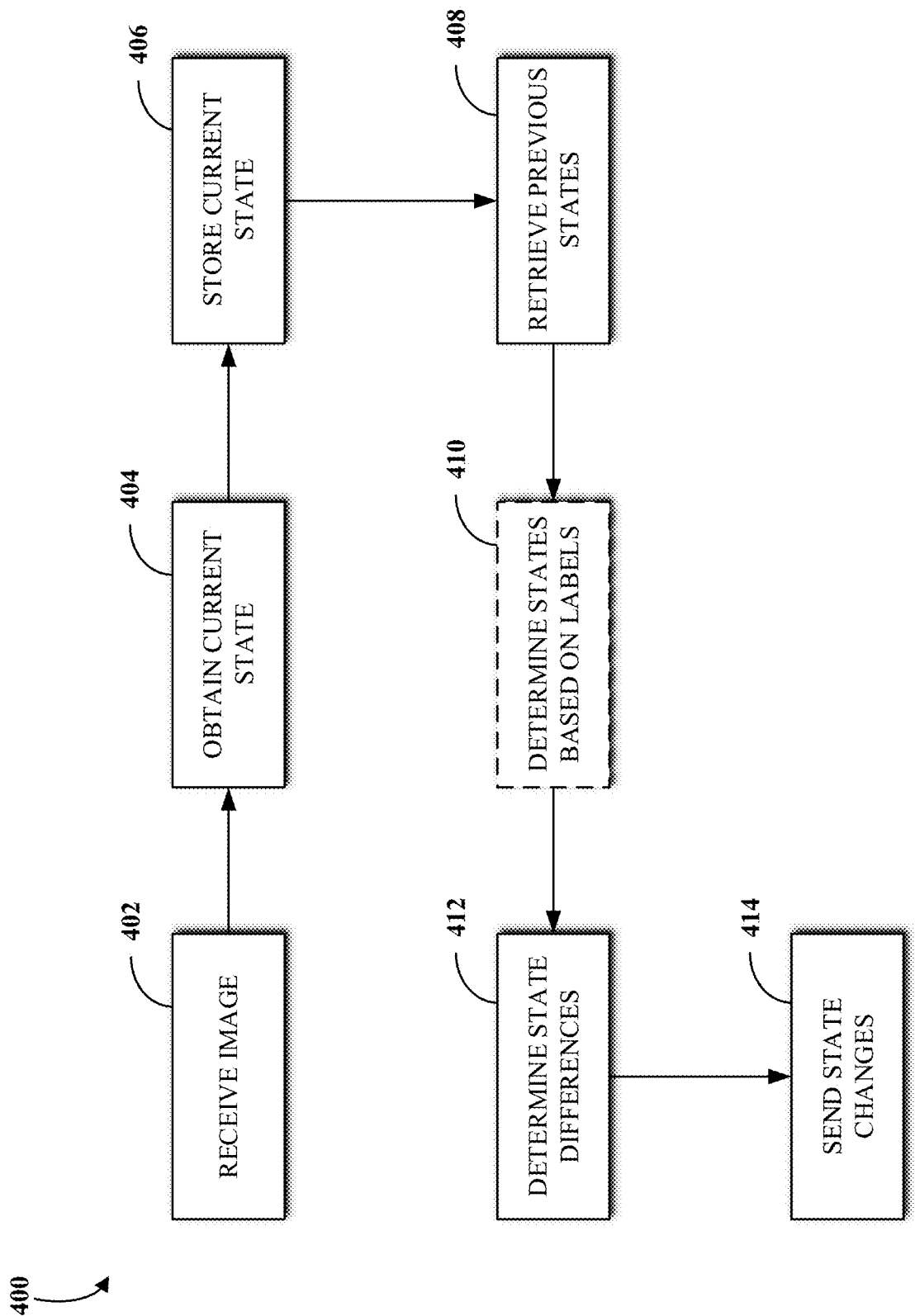
FIG. 4 is an example of flowchart of a technique for state detection according to implementations of this disclosure.

FIG. 4 is an example of flowchart of a technique 400 for state detection according to implementations of this disclosure. The technique 400 can be used to detect the state of a monitored environment and/or a portion therein. The monitored environment can be a hospital room, a portion thereof or therein, such as hospital bed, a chair, and/or other objects or persons therein.

The technique 400 monitors for changes in the state. The technique 400 uses images of the monitored environment captured by a camera (such as a camera of a monitoring device) to detect state changes. Image analysis can be used to detect the states. Upon detecting a change in the state, the technique 400 can send a notification of the state change. The notification can be sent to a server, such as the server 108 of FIG. 1. The monitoring device performing the technique 400 need only send notifications of the state changes to the server (such as for logging or further processing) thereby reducing network traffic.

The technique 400 can be implemented by a monitoring device, such as the monitoring device 104 of FIG. 1 or the monitoring device 300 of FIG. 3, which can be placed in the monitored environment, such as the monitored environment 102 of FIG. 1. The technique 400 can be implemented, partially or fully, by a computing device, such as the computing device 200 of FIG. 2. The technique 400 can be implemented as computer instructions that may be stored in a memory, such as the memory 204 of FIG. 2. The computer instructions can be executed by a processor, such as the processor 202 of FIG. 2. As mentioned above, the monitoring device may not itself include a processor but may be connected to a processor. Thus, the technique 400 can be implemented, partially or fully, by the processor to which the monitoring device is connected.

At 402, the technique 402 receives an image. The image can be received from a camera, which may be part of or is connected to the monitoring device. The image can be a frame of a video stream received from the camera. While not specifically shown in FIG. 4, the technique 400 can be performed on successive images received from the camera. In an example, the camera can be directed, such as by the monitoring device, to capture single images, such as every certain period of time (e.g., 500 milliseconds, 1 second, 2 seconds, or some other period of time). In the case of a video stream, the technique 400 can be carried out on every frame of the video stream. In another example, the technique 400 can be carried out on less than all the frames of the video stream. For example, the technique 400 may process a certain frequency of frames of the video stream, such as every 10th frame, 20th frame, or some other frequency. In an example, at least the images from which state information is obtained can be saved in a memory of the of monitoring device.

At 404, the technique 400 obtains a current state of the monitored environment. In an example, the current state can be obtained as a set of state labels where each state label corresponds to a value of the respective state. The current state labels can be obtained from a ML model, such as a multi-label image classification model.

The current state of the monitored environment (also referred to, simply, as state or room state), as used herein, refers to the collection of individual states, or a subset thereof, to be inferred (e.g., is of interest) and that the ML model is trained to detect. To illustrate, and without loss of generality, with respect to a hospital room that includes a patient bed, the room state can include respective states of one or more of the bed rails, respective states of inclining sections of the bed, a bed sheet state, a food tray state, patient position states, more states, fewer states, other states, or a combination thereof.

The states of one or more of the bed rails describe whether one or more of the bed rails are up (i.e., raised) or down (i.e., lowered). For example, the states of one or more of the bed rails can include respective states for each of the rails (e.g., a top-right rail, a top-left rail, a bottom-right rail, and/or a bottom-left rail). The bed-incline state can include whether the section of the bed supporting the patient's head is up or down. In an example, the bed-incline state can include an estimate of the inclination angle. The bed sheet state can indicate whether the bed sheets are on or off the bed and/or whether the patient is covered or not. The food tray state can indicate whether the food tray is within a threshold distance from the bed. The patient position states can indicate the position of the patient on the bed. That is, on which of his/her body is the patient lying. The patient position states can indicate one or more of whether the patient is lying down on his/her left side, his/her right side, or his/her back, is getting out of the bed, is out of bed, more patient position states, less patient positions, other patient positions, or a combination thereof.

As mentioned above, the ML model can be a multi-label image classification model. In the ML model, an output may be associated with each possible state label. In an example, the ML model can output a first value (e.g., 1, YES, TRUE, etc.) for a label if the state associated with the label is detected in an image; and can output a second value (e.g., 0, NO, FALSE etc.) if the state is not detected. The ML model can be thought of as outputting, for each state (i.e., a label) of the state model, a corresponding value.

To illustrate, and without loss of generality, assume that the room state includes a first state (corresponding to whether the patient is lying on his/her back), a second state (corresponding to whether the patient is lying on his/her left side), and a third state (corresponding to whether the bottom-left rail of the bed is up or down). As such, when an image of the room (e.g., an image of a part of the room) that shows the patient lying on his/her back and the bottom-left rail in the down position is input to the ML model, the ML model outputs the tuple (1, 0, 1) corresponding, respectively, to a first state value (i.e., 1) indicating that the patient is on his/her back, a second state value (i.e., 0) indicating that the patient is not lying on his/her left side, and a third state value (i.e., 0) indicating that the bottom-left rail is in the down position.

The values output by the ML model are not particularly limited. For example, instead of (1, 0, 1), the ML model can output (Yes, No, Yes), ("on back," "not on left side," "down"), (TRUE, FALSE, TRUE), or some other values. In an example, one output label can correspond to several states of the room state. For example, one output can correspond to both the first state (e.g., whether the patient is lying in his/her back) and the second state (e.g., whether the patient is lying in his/her left side). As such, the output label can have the values "back," "left," and "neither;" or some other similar labels. In an example, the outputs of the ML model can be translated into human-readable values (or labels) and only include only those states that are actually identified. For example, instead of the tuple (1, 0, 1), the human readable output can be: Patient_on_bed_back and Bed_rails_bottom_left_down, as described below with respect to Table I. The human readable output can be more descriptive, such as "The patient is on the bed lying on his/her back, and The bottom left rail is down." In an example, the states that are not detected can be omitted from the human readable output. In another example, the values corresponding to all detectable states can be output.

Table I illustrates an example of label classifications that can be detected (e.g., inferred) using the ML model with respect to a monitored environment that is a hospital room. That is, Table I describes an example of the states that the ML model may be trained to detect. It is noted that the disclosure herein is not limited to the states described with respect to Table I and implementations according to this disclosure can infer fewer states, more states, other states, or a combination thereof.

TABLE I

| Label | Description |
| --- | --- |
| Patient_on_bed_back | The patient is on the bed lying on his/her back |
| Patient_on_bed_right | The patient is on the bed lying on his/her right side |

TABLE I-continued

| Label | Description |
| --- | --- |
| Patient_on_bed_left | The patient is on the bed lying on his/her left side |
| Patient_getting_out_bed | The patient is about to get out of bed |
| Patient_on_bed_down | The patient is scooched to the bottom of bed |
| Patient_on_bed_above_rails | The patient is on the bed with limbs over the rails |
| Patient_out_of_bed | The patient is out of the bed |
| Patient_standing | The patient is standing up |
| Patient_on_chair_normal | The patient is sitting on a chair |
| Patient_getting_out_chair | The patient is about to get out of the chair |
| Patient_out_of_chair | The patient is out of the chair |
| Patient_on_floor | The patient is on the floor |
| Staff_in_room | Hospital staff is with the patient |
| Bed_empty | The bed is empty |
| Chair_empty | The chair is empty |
| Bed_inclined | The bed is inclined above 30% |
| Bed_rails_top_right_down | The top right rail is down |
| Bed_rails_top_left_down | The top left rail is down |
| Bed_rails_bottom_right_down | The bottom right rail is down |
| Bed_rails_bottom_left_down | The bottom left rail is down |
| Visitor_in_room | Non-Staff person is in the room |

In another example, the bed rails can be associated with states of being up as opposed to being down. As such, the labels would be Bed_rails_top_right_up, Bed_rails_top_left_up, Bed_rails_bottom_right_up, and Bed_rails_bottom_left_up.

It is noted that at least some of the states (e.g., state labels) may be mutually exclusive while others may not be. For example, the patient cannot be both on the bed lying on his/her back (state label Patient_on_bed_back) and out of bed (state label Patient_out_of_bed) at the same time. Some of the labels can be simultaneously detected in the same image. While binary values are described above as being output from the ML model, in another example, the ML model may be trained to output a confidence level (such as a percent value) for each state. As such, the patient may be inferred to be both on his/her back and out of bed, with different degrees of confidence. In an example, if the confidence level is below a certain confidence threshold (e.g., 30% or some other percent), then the detected state can be ignored.

At 406, the technique 400 stores the current state. In an example, the technique 400 can store the outputs of the ML model. In an example, the technique 400 can store the current state labels corresponding to the output values of the states. A timestamp of obtaining the state can be associated, and stored, with the state. The timestamp can be associated with each of the state values. The timestamp can be the time of receiving the image from the camera, the time that the camera captured the image, the time that the state was obtained at 404, or a combination thereof. The state (e.g., the state labels) and associated timestamp(s) can be stored in a memory, such as the memory 204 of FIG. 2.

At 408, the technique 400 retrieves the last previously saved states from the memory. The last previously saved states are retrieved so that they can be compared to the states obtained in 404. In some situations, last previously saved states may not be available. Such may be the case when the image being processed at 402 is a first image received for the monitored environment. For example, when a new patient is in the room, any stored states may be reset (e.g., archived, deleted, etc.) and obtaining current states at 404 begins anew. For example, when a new monitoring shift for the same patient is started or the monitoring device is reset, there may not be last previously saved states available. As such, the last previously saved states may be an empty state or some value indicating that last previously saved states do not exist.

At 410, in some implementations, the technique 400 may determine at least one state based on labels or states obtained from the image. As further described below with respect to the state of "Reposition," the state cannot be obtained directly from the image. Rather such state is inferred based on further processing (e.g., rules and/or configurations) of the state or state labels obtained from the image. In some implementations, and further described below, the further processing may be performed by/at a server. In some implementations, the monitoring device and the server may perform further processing to infer different states from the states obtained using the ML model.

At 412, the technique 400 determines whether there are any state changes. To illustrate, and without loss of generality, assume that the last previously saved states include the labels Patient_on_bed_back and Bed_inclined, and the current state includes Patient_on_bed_back and Bed_rails_top_left_up. As such, there are state changes corresponding to the labels Bed_inclined and Bed_rails_top_left_up. In the case that last previously saved states do not exist, then the technique 400 determines that there is a change with respect to each of labels of the current state.

At 414, the technique 400 sends a notification of the state changes. In an example, the notification can be sent to a server, such as the server 108 of FIG. 1. In an example a notification may be sent directly to a user device, such as one of the user devices 106 of FIG. 1. In an example, the notification may be sent to a user and received by the user at the user's user device 106.

The server may perform additional processing (e.g., further state detection) based on the received notification. For example, the server may perform additional processing with respect to monitored conditions, as described below). In an example, the server can determine how to handle the state changes based on configurations and settings for alerts, documentation, audit reporting, some other purpose, or a combination thereof.

Figure 5:
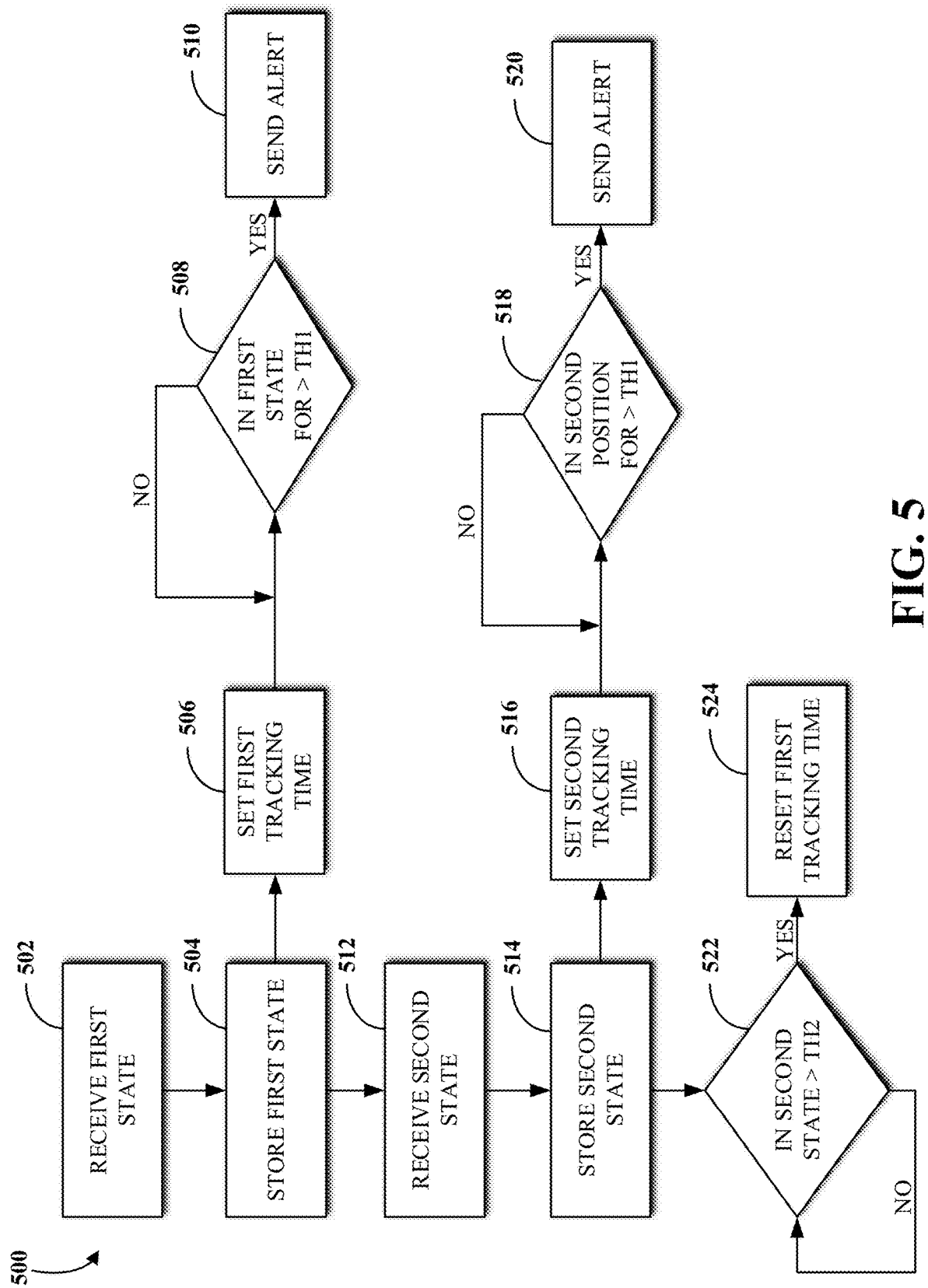
FIG. 5 is an example of flowchart of a technique for handling a monitored condition according to implementations of this disclosure.

FIG. 5 is an example of flowchart of a technique 500 for handling a monitored condition according to implementations of this disclosure. As eluded to above, some of the states can be directly determined by the classification labels of an image or video frame. However some states require further processing.

Such processing can be carried out at a server, such as the server 108 of FIG. 1. In another example, such further processing can be performed at the monitoring device. The technique 500 can be implemented, partially or fully, by a computing device, such as the computing device 200 of FIG. 2. The technique 500 can be implemented as computer instructions that may be stored in a memory, such as the memory 204 of FIG. 2. The computer instructions can be executed by a processor, such as the processor 202 of FIG. 2.

To illustrate, and without loss of generality, a patient is to be monitored to make sure that the patient will not develop bedsores (e.g., a monitored condition). If a patient lies on one side of his/her body (e.g., the back) for more than a threshold time (e.g., two hours), then the patient should be repositioned to another side (e.g., the left side) and must remain on the other side (e.g., the left side) for at least another threshold time (e.g., 15 minutes) before returning to the one side (e.g., the back). If the patient remains on the other side (e.g., the left side) for longer than the threshold time, then the clock resets with respect to developing bedsores. That is, the clock reset with respect to detecting the monitored condition (e.g., detecting for possibility of bedsores) with respect to the patient being on the one side (e.g., the back). If the patient returns to the one side (e.g., the back) within the threshold time (e.g., in less than 15 minutes), then any additional time on the one side (e.g., the back) would be added to the time that the patient was on the one side (e.g., the back) before being repositioned to the other side (e.g., the back). While described, for illustrative purpose, further processing of state changes with respect to bedsores, the disclosure is not so limited and further and other processing is contemplated with respect to other processing and state changes.

Thus, the technique 500, with respect to a monitored condition that is bedsores, can be summarized as getting a last position (i.e., a state) of the patient; adding the time that the patient has been in this state (position); if the position has been in this state for more than a first threshold time (e.g., two hours or some other time), then record a state of "Reposition" as the patient needs to be repositioned to prevent bedsores; and if the patient is in a new position, determine whether the patient has been in the new position for at least a second threshold time (e.g., 15 minutes or some other time) and, if so, reset the tracking times. Recording a state of "Reposition" can include sending an alert, such as to a nurse, to reposition the patient.

At 502, the technique 500 receives a first state. The first state can be received from the monitoring device as described above with respect to FIG. 4. At 504, the technique 500 stores the first state. A timestamp can be stored with the first state. The timestamp can be the time that the first state was received at 502. The timestamp can be received at 502 with the state, as described above.

If the technique 500 determines (not shown) that the first state relates to a monitored condition, then the technique 500 proceeds simultaneously to 506 and 512; otherwise, the technique 500 proceeds only to 512.

At 506, the technique 500 sets a first tracking time (a first timer) for the first state. That is, the technique 500 sets a clock to track the amount of time that the monitored state is set. If a first timer is already associated with (e.g., started for, etc.) the first state, then no new timer is set (e.g., initiated, activated, enabled, etc.). Rather, the first timer can be restarted if the first timer is paused. In an example, the first timer may be paused when a second state is received. In another example, the first timer may not be paused when the second state is received. The first timer is reset as described below with respect to 524 of FIG. 5.

At 508, the technique 500 monitors the duration of the first state. For example, in a continuous manner (e.g., every 30 seconds, 1 minute, 5 minutes, or some other time), the technique 500 determines whether, for example, a current time and the timestamp associated with the first state is greater than a threshold time (TH1). If the first state has been active for more than the threshold time, the technique 500 proceeds to 510; otherwise the technique 500 can sleep until the next time that it performs the block 508. At 510, the technique 500 sends an alert of the state. For example, with respect to the monitored condition being related to bedsores, the alert can be according to the template "the patient has been in the state <state> for more than <TH1>," where <state> and <TH1> are placeholder. As such, the alert can be "the patient has been in the state Patient_on_bed_back for more than 2 hours." The alert can simply be "Reposition the patient." Other alerts are possible. In an example, the technique 500 can regularly resent (not shown) the alert until the technique 500 receives a change in the state.

At 512, the technique 500 receives a second state. The second state can be received from the monitoring device, as described with respect to FIG. 4. If the second state relates to the monitored condition, then the technique 500 proceeds to 516-520, which are similar to 506-510, respectively. For example, the second state can be that the patient is now on his/her right side whereas the first state can be that the patient was on his/her back.

At 522, the technique 500 determines whether the second state has been active for longer than a second threshold time (TH2). If so, then the technique 500 proceeds to 524 to reset the tracking time (e.g., the first timer) associated with the first state. if the technique 500 does not determine that the second state has been active for longer than the second threshold time, then the technique 500 can sleep for a period of time and then return to 522.

Figure 6A:
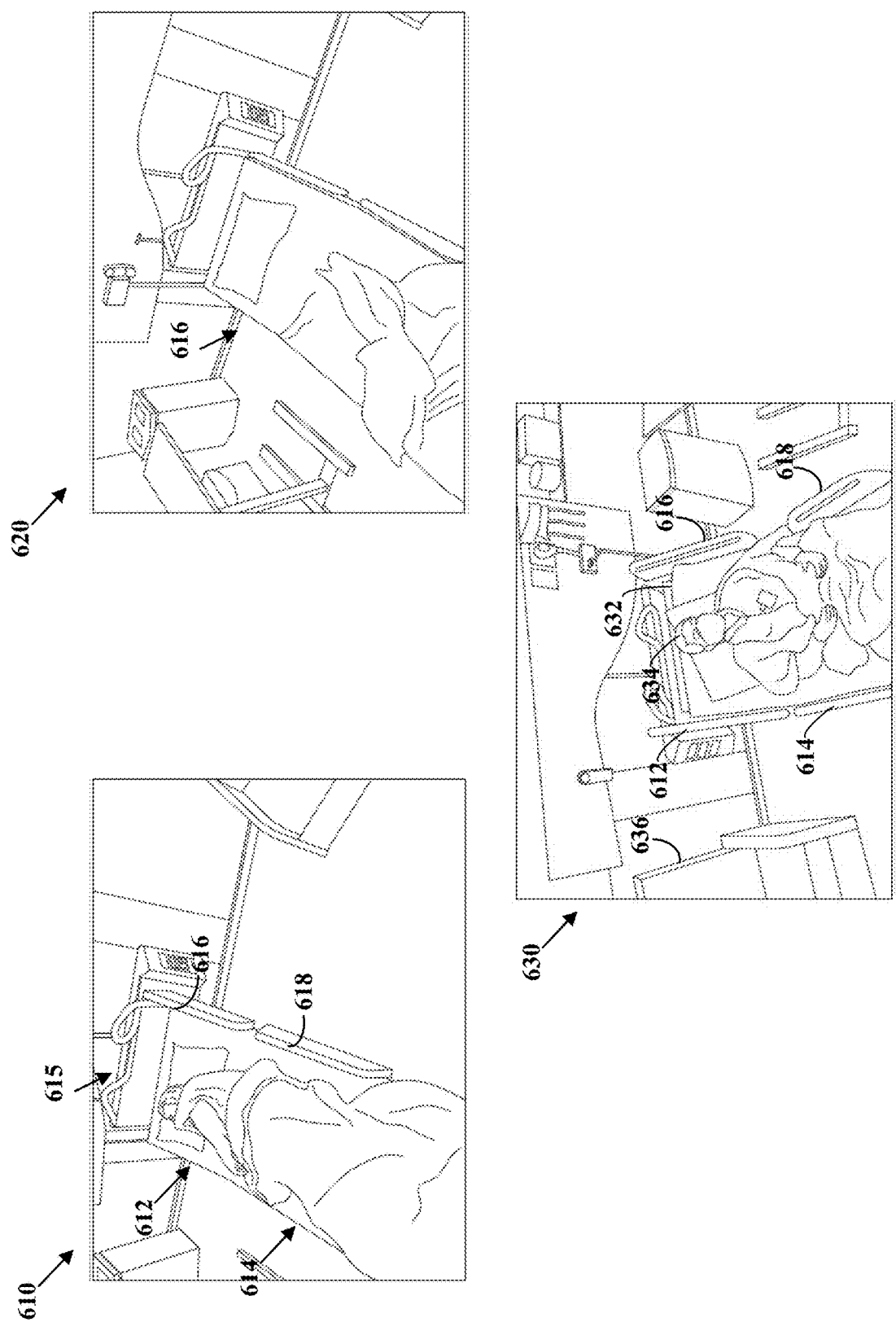
FIGS. 6A-6B illustrate examples of images and corresponding state labels according to implementations of this disclosure.
Figure 6B:
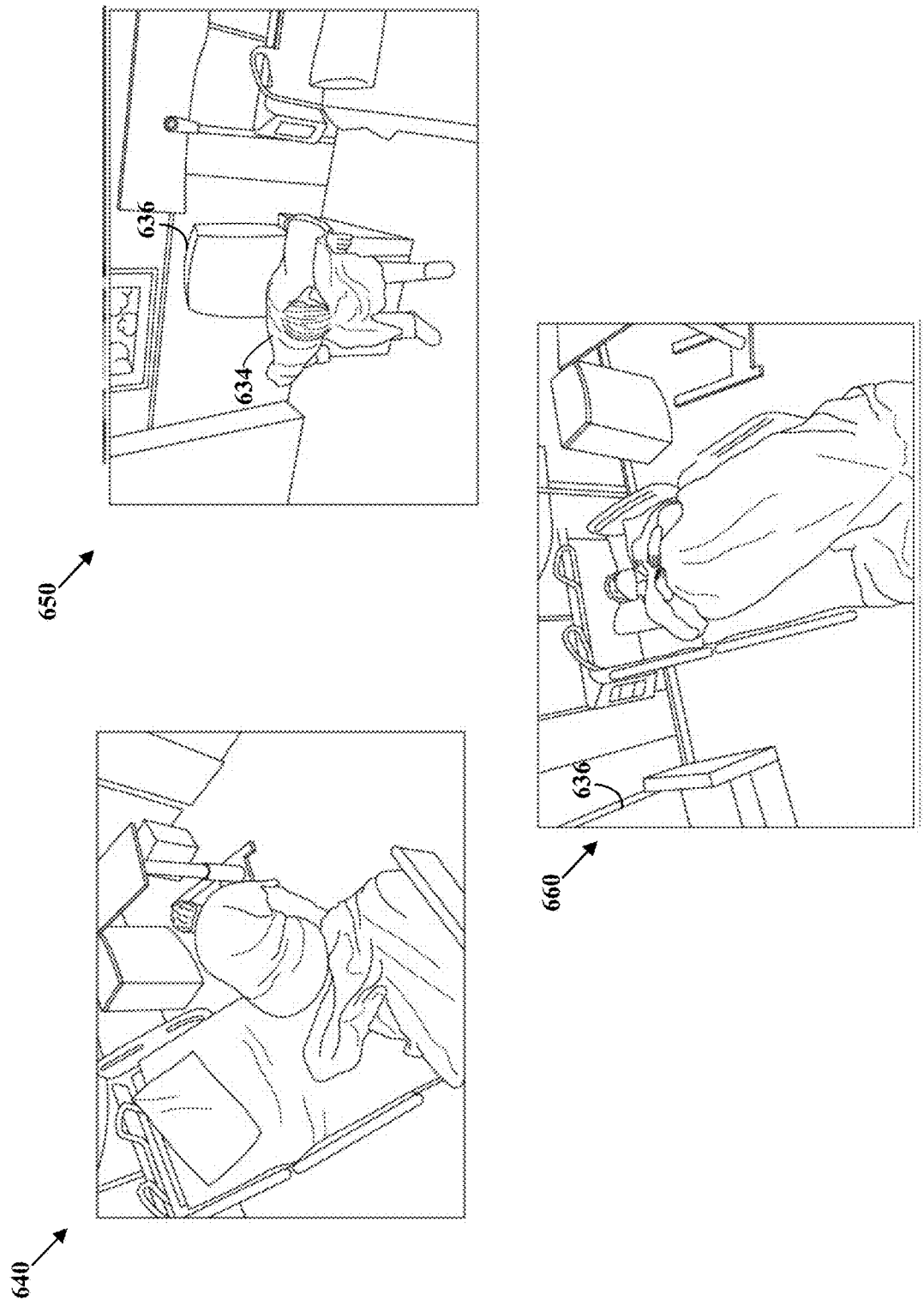

FIGS. 6A-6B illustrate examples of images and corresponding state labels according to implementations of this disclosure. When images 610-660 are presented to a ML model, which is as described above, the ML model can output the indicated labels of Table I.

With respect to the image 610, at least the labels Patient_on_bed_right, Bed_rails_top_right_down, and Bed_rails_bottom_right_down. As is shown in the image 610, a top-right rail 612 and a bottom-right rail 614 of a bed 615, and which are hidden from view, are down. On the other hand, a top-left rail 616 and a bottom-left rail 618 of the bed 615 are up. With respect to the image 620, at least the label Bed_empty is output because the patient is not in the bed 615.

With respect to the image 630, at least the labels Bed_inclined (because a head-support section 632 is inclined up over 30 degrees), Patient_on_bed_back (because a patient 634 is lying on his back), and Chair_empty (because, even though a chair 636 is partially in the image 630, the ML model infers that it is empty) are output. If the bed rail states are described in terms of whether they are up, as mentioned above, then the ML model would output the labels Bed_inclined, Patient_on_bed_back Bed_rails_top_right_up, Bed_rails_top_left_up, Bed_rails_bottom_right_up, Bed_rails_bottom_left_up, and Chair_empty because the top-right rail 612, the bottom-right rail 614, the top-left rail 616, and the bottom-left rail 618 are all in the up (i.e., raised) position.

With respect to the image 640, at least the labels Patient_getting_out_bed and Bed_rails_bottom_left_up are output. Alternatively, if the bed rail states are described in terms of whether they are up, then the labels Patient_getting_out_bed, Bed_rails_top_right_up, Bed_rails_top_left_up, and Bed_rails_bottom_right_up can be output. With respect to the image 650, at least the label Patient_getting_out_chair is output. With respect to the image 660, at least the labels Patient_on_bed_back and Chair_empty may be output.

Figure 7:
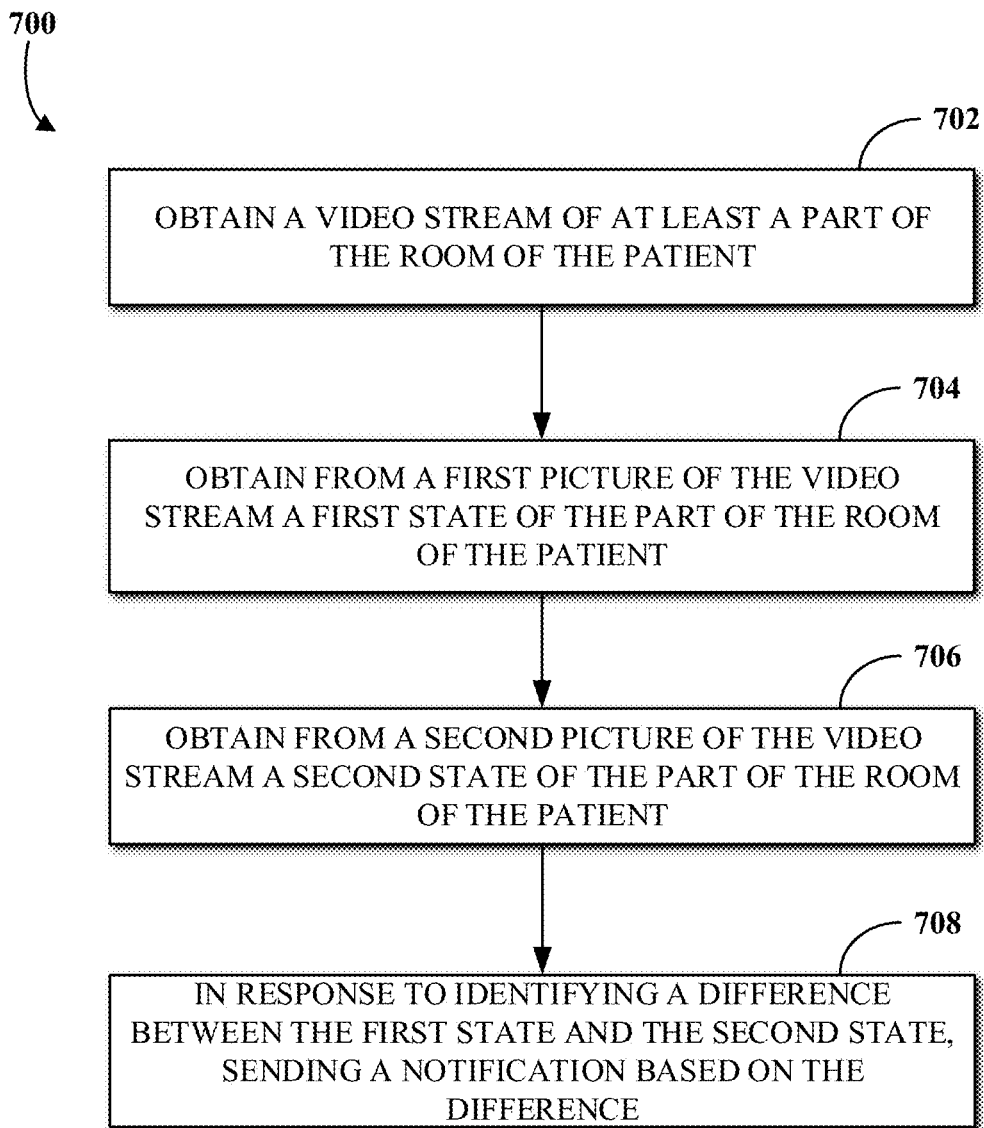
FIG. 7 is an example of flowchart of a technique for monitoring a room of a patient according to an implementation of this disclosure.

FIG. 7 is an example of flowchart of a technique 700 for monitoring a room of a patient according to an implementation of this disclosure. The technique 700 can be used to detect the state of a hospital room of the patient or a portion therein.

The technique 700 monitors for changes in the state. The technique 700 uses images of the room, which are captured by a camera (such as a camera of a monitoring device), to detect state changes. Image analysis can be used to detect the states. The image analysis can be performed by a ML model, which can be a multi-label classification model. Upon detecting a change in the state, the technique 700 can sent a notification of the state change. The notification can be sent to a server, such as the server 108 of FIG. 1. The monitoring device performing the technique 700 need only send notifications of the state changes to the server (such as for logging or further processing) thereby reducing network traffic.

The technique 700 can be implemented by a monitoring device, such as the monitoring device 104 of FIG. 1 or the monitoring device 300 of FIG. 3, which can be placed in the monitored environment, such as the monitored environment 102 of FIG. 1. The technique 700 can be implemented, partially or fully, by a computing device, such as the computing device 200 of FIG. 2. The technique 700 can be implemented as computer instructions that may be stored in a memory, such as the memory 204 of FIG. 2. The computer instructions can be executed by a processor, such as the processor 202 of FIG. 2. As mentioned above, the monitoring device may not itself include a processor but may be connected to a processor. Thus, the technique 700 can be implemented, partially or fully, by the processor to which the monitoring device is connected.

At 702, the monitoring device obtains a video stream of at least a part of the room of the patient. In an example, the video stream may be a sequence of images that are captured at regular time intervals. At 704, the monitoring device obtains from a first picture of the video stream a first state of the part of the room of the patient. As described above, the first state can include respective states associated with different aspects of the room. As such, the first state can include states related to the patient, different parts of the patient's bed, and so on as described above.

At 706, the monitoring device obtains, from a second picture of the video stream, a second state of the part of the room of the patient. The second state can be as described with respect to the first state. At 708, in response to identifying by the monitoring device a difference between the first state and the second state, the technique 700 sends a notification based on the difference, such as described with respect to FIG. 4.

In an example, the first state and the second state can each be obtained using a multi-label picture classification model, as described above. In an example, the first state or the second state can include at least one of bed-rail states, bed-incline states, or patient-position states. The bed-rail states can include respective states indicating positions of a top right rail, a top left rail, a bottom right rail, or a bottom left rail. In an example, the patient-position states can include respective states indicating whether the patient is lying down on a left side of the patient, whether the patient is lying on a right side of the patient, whether the patient is lying on a back of the patient, whether the patient is getting out of a bed, or whether the patient is out of the bed.

In an example, and as described with respect to FIG. 5, the technique 700 can further include setting a monitored condition of the patient based on the first state; and resetting the monitored condition in response to determining that the second state persists for a threshold time. In an example, the monitored condition can relate to bedsores.

In an example, the technique 700 can store images from which state information is obtained (i.e., images that are input to the ML model) in a memory of the monitoring device. The images can be stored in association with the state. For example, and referring to FIG. 4 again, the image can be stored at 406. In an example, one or more of the stored images can be retrieved from the storage. For example, in response to a request (such as from a server and/or a user device) for a state stored at or within a certain time, the corresponding image(s) may also be returned to the requestor.

Another aspect of the disclosed implementations includes a system that includes a server and a monitoring device. The monitoring device can be configured to obtain, at a first time, a first image of at least a part of the room; identify a first state of the patient based on first image; obtain at a second time a second image of the at least the part of the room; identify a second state of the patient based on the second image; and, in response to the first state being different from the second state, send a first notification to the server. The server can be configured to, in response to receiving the first notification, set a monitored condition of the patient to a first value.

In an example, the monitored condition can relate to bedsores, the first state can indicate whether the patient is lying on a first body side, and the second state can indicate whether the patient is lying on a second body side that is different from the first body side.

In an example, the server can be further configured to, in response to the monitored condition having the first value for more than a threshold amount of time, send an alert. In an example, the server can be further configured to receive a second notification that includes a third state of the patient obtained at a third time; and determine whether to set the monitored condition to a second value based on whether a time difference between the first time and the third time exceeds a threshold.

In an example, the system can further include a user device that is configured to display changes over time of at least one of the first state or the second state.

Figure 8:
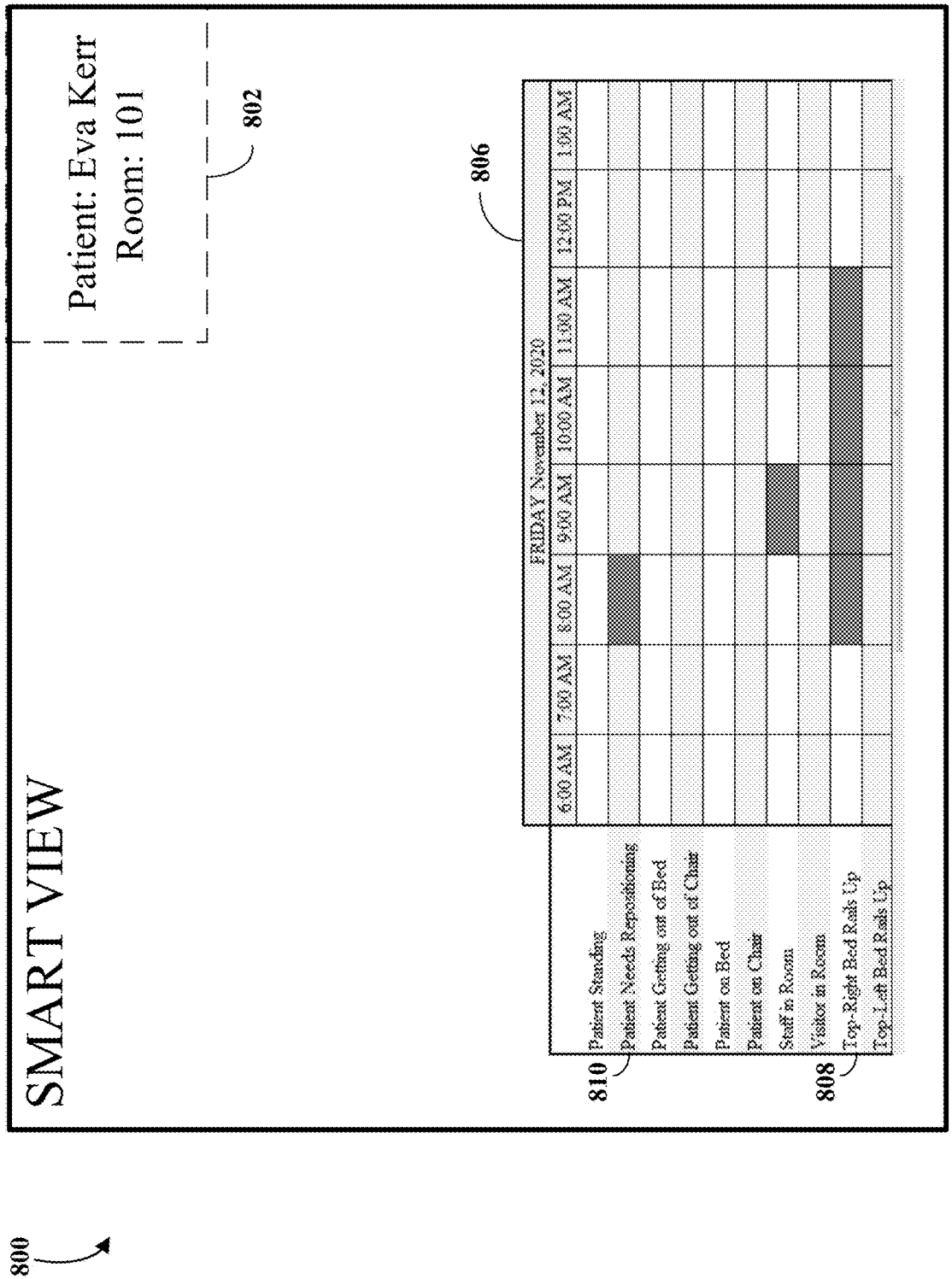
FIG. 8 is an example of a display of state information according to implementations of this disclosure.

FIG. 8 is an example of a display 800 of state information according to implementations of this disclosure. The display 800 can be displayed on a user device, such as the user device 106 of FIG. 1. For example, the display 800 can be displayed on a display at a nurses station. The display 800 can be generated based on the state change information received by a server, such as the server 108 of FIG. 1. In an example, a user action at the user device can cause the display 800 to be generated at the server and displayed at the user device. While the display 800 of FIG. 8 includes certain information and has a certain layout, the disclosure herein is not so limited and a display according to implementations of this disclosure can include more, fewer, other information, or a combination thereof and/or can have a different layout.

The display 800 includes identification information 802, which can include the name of the patient for whose room state information is being displayed. The display 800 includes an abstract view 803 of the room of the patient. The abstract view 803 can be displayed instead of a real image of the room for privacy reasons. In another example, actual images captured by the camera of the monitoring device can be displayed in the display 800. The abstract view 803 can be generated from one or more templates corresponding to different states. For example, if the state obtained from the ML model includes the labels Patient_out_of_bed, Bed_inclined, and Chair_empty, then the abstract view 803 can include an image template 804 of a bed that is empty and inclined and an empty chair template 805. The image templates that used can be layout out according to the actual arrangement in the actual image.

The display 800 includes a history 806. The history 806 can be a scrollable table that displays the room states over time, which are saved by the server. The history 806 of the display 800 has a unit of measure of 1 hour. However, a user of the display 800 can zoom in and out to show more granular (e.g., down to the minute or less) or coarser state information. In an example, the history 806 can include a row for each of the states (e.g., labels) that can be obtained from the ML model. The history 806 can include rows for states that are further determined by the server based on the state changes received (i.e., states that require server processing, such as described with respect to FIG. 5). The time periods during which the state was detected can be highlighted in the history 806. For example, a row 808 shows that the Top-Right Bed Rails were up (i.e., the label Bed_rails_top_right_up) from 8:00 AM to 12:00 PM; and a row 810 shows that the patient needed repositioning during the 8:00 AM hour. The patient could have needed repositioning for reasons described with respect to FIG. 5.

The abstract view 803 can be displayed based on the particular time point selected by the user. In an example, the display 800 can be automatically updated, such as when a state change is received at the server. The display 800 can be updated according to the state change information. In an example, the display 800 can include video-player-like controls allowing the user to play, rewind, or pause the display 800. For example, the user may click to select 8:00 AM in the history 806 and then select the play control. The abstract view 803 can then update to display views corresponding to the state changes starting at 8:00 AM.

Figure 9:
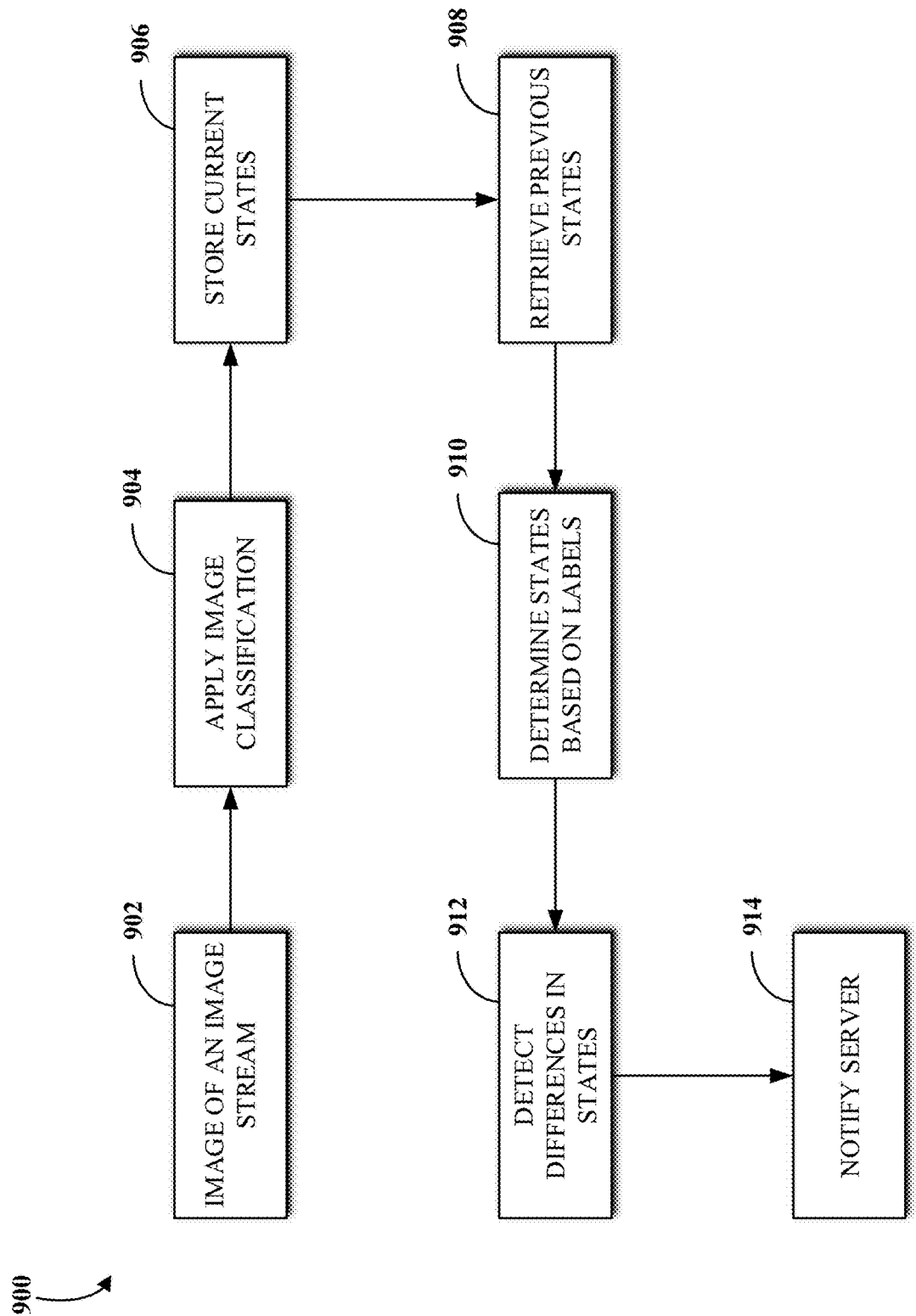
FIG. 9 is an example of flowchart of a technique for monitoring a room of a patient according to implementations of this disclosure.

FIG. 9 is an example of flowchart of a technique 900 for monitoring a room of a patient according to implementations of this disclosure. The technique 900 can be used to detect active states (e.g., conditions of interest) relating to the patient room, objects therein, the patient, other persons therein, or other aspects of the patient room (collectively, and for brevity, active states of the patient room). Detecting an active state can mean identifying (e.g., determining, inferring, etc.) that a state of interest has changed from an inactive state (e.g., not detected) to active (e.g., detected).

The technique 900 can detect the active states by examining images of an image stream of the patient room. An active state can be a condition of interest regarding the patient room such that the condition was not detected in an examined image of the image stream but is detected in a next immediate image to be examined. In an example, examining an image can mean using the image as an input to a machine learning model, as described herein. While the technique 900 is described with respect to monitoring a room of a patient, the technique 900 can be used to monitor any type of environment to be monitored.

The technique 900 monitors for changes in the state. The technique 900 uses images of the monitored environment captured by a camera (such as a camera of a monitoring device) to detect active and persistent states. Image analysis can be used to detect the active and persistent states. Upon detecting an active or a persistent state, the technique 900 can send a notification of the active or persistent state. The notification can be sent to a server, such as the server 108 of FIG. 1. The monitoring device performing the technique 900 need only send notifications of the active or persistent state to the server thereby reducing network traffic and reducing human overload, as described herein.

The technique 900 can be implemented by a monitoring device, such as the monitoring device 104 of FIG. 1 or the monitoring device 300 of FIG. 3, which can be placed in the monitored environment, such as the monitored environment 102 of FIG. 1. The technique 900 can be implemented, partially or fully, by a computing device, such as the computing device 200 of FIG. 2. The technique 900 can be implemented as computer instructions that may be stored in a memory, such as the memory 204 of FIG. 2. The computer instructions can be executed by a processor, such as the processor 202 of FIG. 2. As mentioned above, the monitoring device may not itself include a processor but may be connected to a processor. Thus, the technique 900 can be implemented, partially or fully, by the processor to which the monitoring device is connected.

At 902, the technique 900 receives an image. The image can be received from a camera, which may be part of or is connected to the monitoring device. The image can be an image of image stream received from the camera. While not specifically shown in FIG. 4, the technique 900 can be performed on successive images of the image stream received from the camera. In an example, the camera can be directed, such as by the monitoring device, to capture single images, such as every certain period of time (e.g., 500 milliseconds, 1 second, 2 seconds, or some other period of time). In the case that the image stream is a video stream (e.g., images captured at a rate of 24 frames per second or some other rate), the technique 900 can be carried out on every frame of the video stream. In another example, the technique 900 can be carried out on less than all the frames of the video stream. For example, the technique 900 may process a subset of the images of the video stream, such as every $10^{th}$ frame, $20^{th}$ frame. In an example, at least the images from which state information is obtained can be saved in a memory of the of monitoring device.

At 904, the technique 900 applies image classification to an image to obtain current states of the monitored environment. Obtaining current states means obtaining state values of the states. In an example, the current states (i.e., the values of the current states) can be obtained as a set of state labels where each state label corresponds to a value of a respective monitored condition (i.e., the monitored state). The current state labels can be obtained from an ML model, such as a multi-label image classification model, which can be as described herein.

The current states of the monitored environment (also referred to, simply, as state or room state), as used herein, refer to the collection of individual states, or a subset thereof, to be inferred (e.g., is of interest) and that the ML model is trained to detect. As mentioned above, the ML model can be a multi-label image classification model. In the ML model, an output may be associated with each possible state label. In an example, the ML model can output a first value (e.g., 1, YES, TRUE, etc.) for a label if the state associated with the label is detected in an image; and can output a second value (e.g., 0, NO, FALSE etc.) if the state is not detected. The ML model can be thought of as outputting, for each state of the state model, a corresponding value (i.e., a label).

To illustrate, and without loss of generality, assume that the current states include a first state (corresponding to whether the patient is sitting down), a second state (corresponding to whether the patient is lying down), and a third state (corresponding to whether the patient is getting up from sitting or lying down). As such, when an image of the room (e.g., an image of a part of the room) that shows the patient lying down, the ML model outputs the tuple (0, 1, 0).

The values output by the ML model are not particularly limited. For example, instead of (0, 1, 0), the ML model can output (No, Yes, No), ("not sitting down," "lying down," "not getting up"), (FALSE, TRUE, FALSE), or some other values. In an example, the outputs of the ML model can be translated into human-readable values (or labels) and only include only those states that are actually identified. For example, instead of the tuple (0, 1, 0), the human readable output can be: "Lying down," as described below with respect to Table II. The human readable output can be more descriptive, such as "The patient is lying down on the bed." In an example, the states that are not detected can be omitted from the human readable output. In another example, the values corresponding to all detectable states can be output.

Table II illustrates an example of state (and corresponding label classifications) that can be detected (e.g., inferred) using the ML model with respect to a monitored environment that is a hospital room. That is, Table II describes an example of the states that the ML model may be trained to detect. More accurately, Table II describes the active states corresponding to monitored states. The states can be easily deduced from Table II and are not specifically described herein. For example, it can be easily inferred from the state label Patient_not_visible that the state is, or corresponds, to whether the patient is visible. It is noted that the disclosure herein is not limited to the state labels described herein and implementations according to this disclosure can infer fewer states, more states, other states, or a combination thereof. In an example, the ML can be trained to detect at least some of the states of the union of the states of Table I and Table II.

TABLE II

| Label | Description |
| --- | --- |
| Patient_Stationary_on_Bed | The patient is in the same previously detected position |
| Patient_not_visible | The patient is not visible |
| Others_in_Room | There are multiple people in the room |
| Patient_Drinking | The patient is drinking |
| Patient_Eating | The patient is eating |
| Patient_Getting_up | The patient is about to get up from sitting or lying down |
| Patient_Lying_Down | The patient is lying down on the bed |
| Patient_Nude | The patient seems to be partially or fully nude |
| Patient_on_Floor | The patient has fallen down |
| Patient_Sitting | The patient is sitting down |
| Patient_Standing | The patient is standing up |
| Patient_Walking | The patient is walking |
| Patient_Waving | The patient is waving at the camera |
| Unknown | The ML model could not identify any states |

With respect to the Patient_Stationary_on_Bed state, one or more previous images may also be used as input to the ML model in additional to a current image. The ML model can be trained to output whether the patient is still in the same position as in the one or more previous images.

It is noted that at least some of the states (e.g., state labels) may be mutually exclusive while others may not be. For example, the patient cannot be both lying down (state label Patient_Lying_Down) and not in view (state label Patient_not_visible) at the same time. Some of the labels can be simultaneously detected in the same image. In an example, the ML model may be trained to output a confidence level (such as a percent value) for each state. As such, the patient may be inferred to be both on his/her back and out of bed, with different degrees of confidence. In an example, if the confidence level is below a certain confidence threshold (e.g., 30% or some other percent), then the detected state can be ignored.

At 906, the technique 900 stores the current detected states. The technique 900 can store the outputs of the ML model. For example, the technique 900 can store the current state labels corresponding to the output values of the states. In an example, a timestamp of obtaining the current states can be associated, and stored, with the states. The timestamp can be associated with each of the state values. The timestamp can be the time of receiving the image from the camera, the time that the camera captured the image, the time that the state was obtained at 904, or a combination of timestamps thereof. The states (e.g., the state labels or state values) and associated timestamp(s) can be stored in a memory, such as the memory 204 of FIG. 2.

At 908, the technique 900 retrieves the last previously saved states (e.g., state values) from the memory. The last previously saved states are retrieved so that they can be compared to the states obtained in 904. In some situations, last previously saved states may not be available. Such may be the case when the image being processed at 902 is a first image received for the monitored environment. For example, when a new patient is in the room, any stored states may be reset (e.g., archived, deleted, etc.) and obtaining current states at 904 begins anew. For example, when a new monitoring shift for the same patient is started or the monitoring device is reset, there may not be last previously saved states available. As such, the last previously saved states may be an empty state or some value indicating that last previously saved states do not exist.

As mentioned above, some conditions of interest can include a temporal element. That is, the conditions (e.g., states) may be identified as active states if they persist for respective durations of time. For example, a state may include whether the patient has moved within the last two hours. As mentioned above, if this state is active, then the patient should be repositioned to prevent bedsores. For example, a state may include whether the patient has not been detected in the images for a specified duration of time (e.g., 15 minutes or some other duration of time). As the patient may have fallen (such as in the bathroom), it is critical to identify such an active state.

In an example, the ML model may have an architecture that includes a memory, such a recurrent neural network, which can be trained to identify a state as active if the state persists for a duration of time. In another example, a respective time duration can also be associated with at least some of the states. The technique 900 can reset to zero the time duration associated with a state responsive to the value output by/from the ML model being different from the immediately preceding output for the state. The technique 900 can add the time between the immediately preceding output and a current output to the time duration. For example, assume that images are processed at time steps of Δt and that at times 0, Δt, 2Δt, 3Δt, and 4Δt the patient was detected to be visible, visible, visible, not visible, and not visible, respectively, of the state "is the patient visible." As such, at the time 2Δt, a total duration of 2Δt can be associated with the value Patient_not_visible; at time 3Δt, the total duration of the Patient_not_visible value is reset to zero; and at time 4Δt, a total duration of 2Δt can be associated with a value Patient_visible of the state "is the patient visible."

At 910, in some implementations, the technique 900 may determine at least one state based on labels or states obtained from the image and the stored states. As described herein, whether a state is active may not be directly obtained directly from the image. Rather such state is inferred based on further processing (e.g., rules and/or configurations) of the state or state labels obtained from the image.

At 912, the technique 900 determines whether there are any state changes. To illustrate, and without loss of generality, assume that the last previously saved states include the labels Patient_Sitting, and the current state includes Patient_Sitting and Patient_Drinking. As such, there are state changes corresponding to the labels Patient_Drinking. In the case that last previously saved states do not exist, then the technique 900 determines that there is a change with respect to each of labels of the current state. Additionally, the technique 900 determines whether persistent states are identified by examining the total durations associated with monitored states with the respective stored durations.

At 914, the technique 900 sends a notification of the state changes. More specifically, the technique 900 sends notification of detected active states or persistent states. In an example, the notification can be sent to a server, such as the server 108 of FIG. 1. In an example a notification may be sent directly to a user device, such as one of the user devices 106 of FIG. 1. The notification can include an image of the monitored environment. The image can be the image that caused the active states or persistent states to the detected. The notification can include the image processed at 902. In another example, the technique 900 can obtain a another image from the camera and transmit the new image in the notification. In an example, the technique 900 can transmit, in the notification, the active and the persistent states identified. In an example, the notification can be transmitted to a user device, such as the user device 106 of FIG. 1. From the perspective of the server and the user device, there may not be any distinction between an active state and a persistent state. As such, and for brevity, an active state and a persistent state are both referred to as active state. As such, in the case that of a persistent state, the technique 900 can be to transmit an active state to the server.

The server may perform additional processing (e.g., further state detection) based on the received notification. For example, the server may perform additional processing with respect to monitored conditions, as described below). In an example, the server can determine how to handle the state changes based on configurations and settings for alerts, documentation, audit reporting, some other purpose, or a combination thereof.

The server can transmit the notification to the user device. In an example, the server can transmit instructions to the user device to display at least one of the image or the active state on a display of the user device. The instructions can includes instructions to highlight the image on the display of the user device.

In an example, if an image is classified as including nudity (e.g., that the patient seems to be partially or fully nude), then the monitoring device can blur (or obscure) at least the private parts of the patient in the image before storing or transmitting the image. In an example, if the server receives an image with an active state of Patient_Nude, the server may blur (or obscure) the at least the private parts of the patient in the image (even if the monitoring device already blurred (or obscured) the private parts of the patient.

Figure 10:
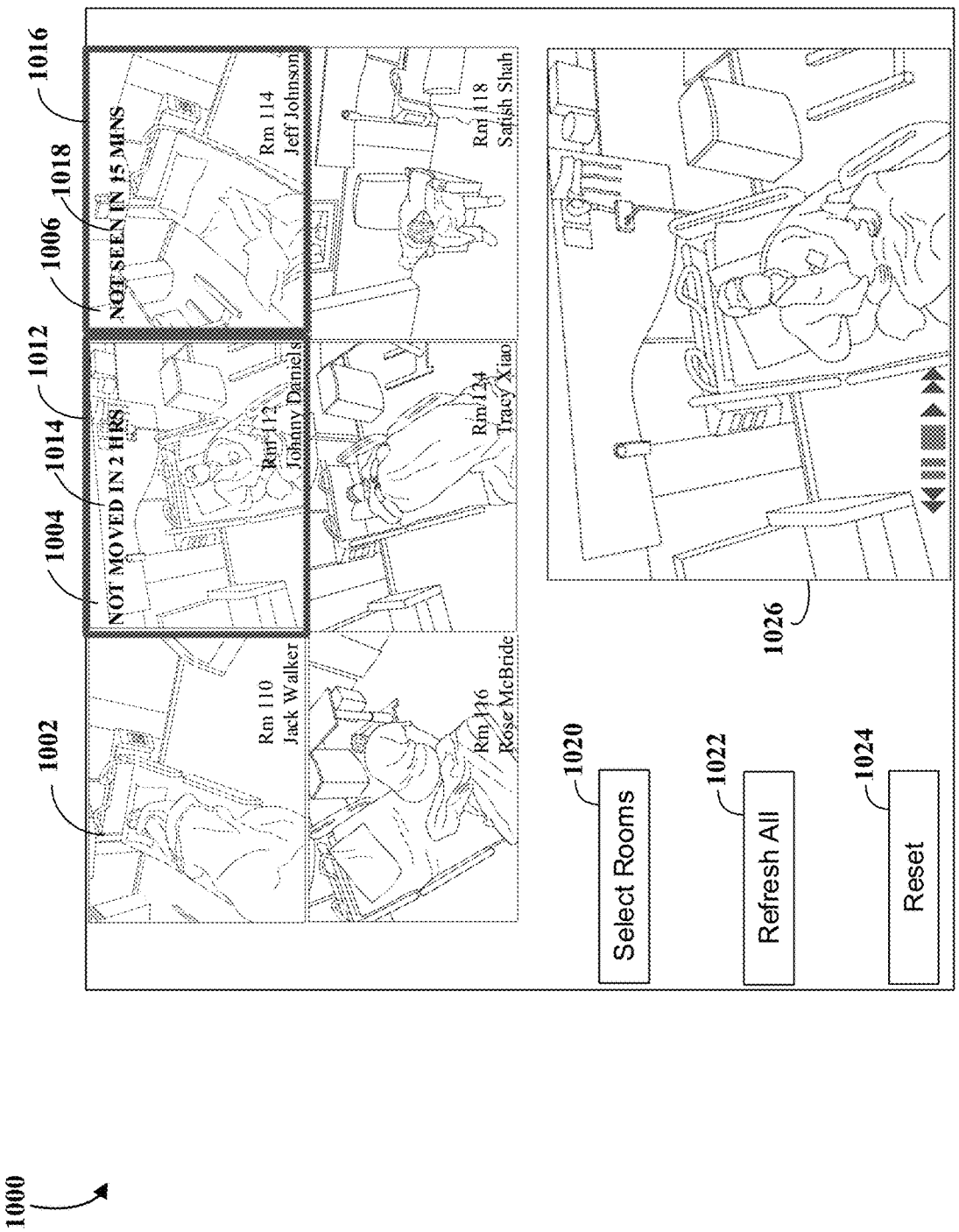
FIG. 10 is an example of a user interface for attention focusing for multiple patients monitoring according to implementations of this disclosure.

FIG. 10 is an example of a user interface 1000 for attention focusing for multiple patients monitoring according to implementations of this disclosure. The user interface 1000 can be displayed on a display of a user device, such as the user device 106 of FIG. 1. The user interface 1000 displays images of patient room, such as images 1002 (patient room number 110), 1004 (patient room number 112), 1006 (patient room number 114).

The user interface 1000 illustrates that the user device received instructions to display notifications related to the patient room numbers 112 and 114 (i.e., image 1004 and 1006, respectively). As mentioned, in an example, the instructions can be received from the server. In another example, notifications can be received from the monitoring devices of respective patient rooms (i.e., the monitoring devices in the patient rooms numbered 112 and 114).

The image 1004 is the image that the technique 900 executing in the monitoring device of the patient room number 112 transmitted in response to detecting an active state (i.e., that the patient has not moved in 2 hours). In an example, an indication or a description of the active state can be displayed in the user interface 1000. In an non-limiting example, the indication or the description of the active can be overlayed on the image, as shown with respect to an active state description 1014. Other ways of displaying or indicating the active states in the user interface 1000 are possible.

The image 1006 is the image that the technique 900 executing in the monitoring device of the patient room number 114 transmitted in response to detecting an active state (i.e., that the patient has not moved in 2 hours). An active state description 1018 is shown as overlaid on the image 1006.

To focus the attention of the user monitoring the user interface 1000, the images 1004 and 1006 can be highlighted. In an example, the highlight can be a solid border that is displayed around an image to be highlighted, such as borders 1012 and 1016. In another example, the border can be a blinking border. In an example, the highlight can depend on the active state. For example, different border colors may be used for different active states. Other ways to draw the attention of the user to newly updated (e.g., received and displayed images) are possible.

In an example, the highlight may persist for a predefined period of time (e.g., 10 seconds, 15 seconds, or some other time). In another example, the highlight persists until cleared by the user. For example, the user may single click on an image to disable (e.g., hide, turn off, etc.) the highlight of the image. Other ways of disabling a highlight of an image are possible. In an example, a reset user interface component 1024 may be available, which, when pressed, disables all highlights on all images.

In an example, the user can obtain an image from a patient room. For example, in response to double clicking the image 1004 (or some other user interface action), an image feed can be displayed in a window 1026. In another example, the image feed can be displayed in place of the image 1004. While not specifically shown in FIG. 10, the user may be able to display multiple image feeds in the user interface 1000. An image feed from a patient room can be received from the monitoring device of that patient room. In an example, the user device can receive the image feed from the monitoring device via peer-to-peer communications. In another example, in response to a user action, the user device sends a request for the image feed to the server. The server can in turn request the image feed from the monitoring device. The server then transmits the image feed to the user device.

In an example, the user interface 1000 can include a control 1020 and a control 1022. In other examples, the user interface 1000 can include other controls. In response to the user exercising (e.g., pressing, clicking, etc.) the control 1020, a list of all rooms that the user can monitor may be displayed and the user can select the rooms for which monitoring images are be displayed in user interface 1000. In response to the user exercising the control 1022, all highlights on all images of the user interface 1000 can be disabled.

Figure 11:
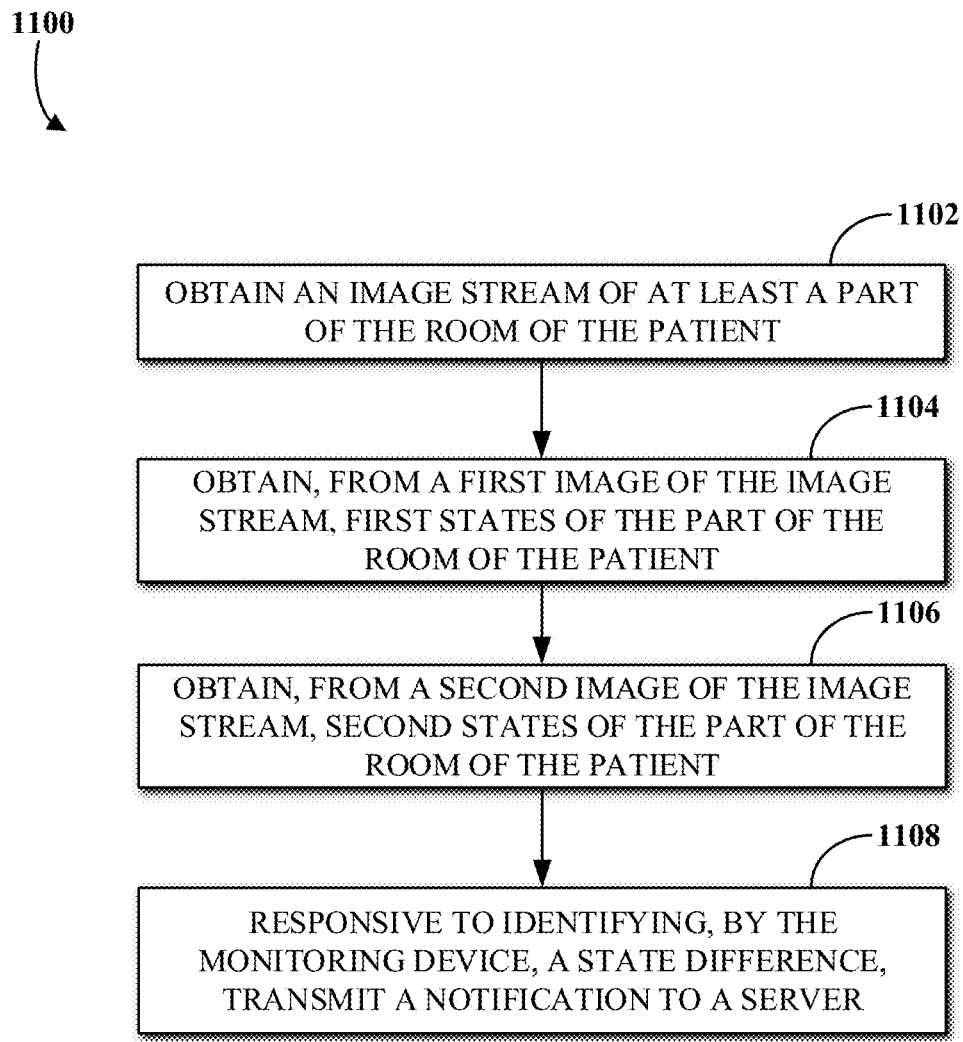
FIG. 11 is an example of flowchart of a technique for monitoring a room of a patient according to an implementation of this disclosure.

FIG. 11 is an example of flowchart of a technique 1100 for monitoring a room of a patient according to an implementation of this disclosure. The technique 1100 detects active and persistent states of the room of the patient or a portion thereof. The technique 1100 uses images of the room, which can be captured by a camera (such as a camera of a monitoring device), to detect state changes. Image analysis can be used to detect the active and persistent states. The image analysis can be performed by a ML model, which can be a multi-label classification model. Upon detecting a change in the state, the technique 1100 can sent a notification of the state change. The notification can be sent to a server, such as the server 108 of FIG. 1. The monitoring device performing the technique 1100 need only send notifications of the state changes to the server (such as for logging or further processing) thereby reducing network traffic.

The technique 1100 can be implemented by a monitoring device, such as the monitoring device 104 of FIG. 1 or the monitoring device 300 of FIG. 3, which can be placed in the monitored environment, such as the monitored environment 102 of FIG. 1. The technique 1100 can be implemented, partially or fully, by a computing device, such as the computing device 200 of FIG. 2. The technique 1100 can be implemented as computer instructions that may be stored in a memory, such as the memory 204 of FIG. 2. The computer instructions can be executed by a processor, such as the processor 202 of FIG. 2. As mentioned above, the monitoring device may not itself include a processor but may be connected to a processor. Thus, the technique 1100 can be implemented, partially or fully, by the processor to which the monitoring device is connected.

At 1102, the monitoring device obtains an image stream of at least a part of the room of the patient. The image stream can be as described above. The technique 1100 can process (e.g., use, etc.) images of the image stream, as they are received, to identify active and persistent states, as described herein.

At 1104, the technique 1100 obtains, from a first picture of the image stream, first states of the part of the room of the patient. As described above, the first states can include, or can mean, respective state values associated with different aspects of the room. As such, the first states can include state values related to the patient (e.g., a state of the patient or an activity of the patient), different parts of the bed of the patient, other persons in the room, and so on, as described above.

At 1106, the monitoring device obtains, from a second picture of the image stream, second states of the part of the room of the patient. The second states can be as described with respect to the first states. At 1108, responsive to identifying a state difference between the first states and the second states, transmitting a first notification to a server. The first notification can include the second image and the state difference, such as described with respect to FIG. 9. The state difference, as used herein, refers to active or persistent states. For example, and as described above, and with respect to the state of whether the patient is waving, an active state may be that the patient is waving. If the patient is subsequently detected to not be waving, which is change from the previous value of the state, the change is not identified as a state difference that is transmitted to the server.

In an example, the first states and the second states can each be obtained using a multi-label image classification model, as described above. In an example, the first states and the second states can each include at least one of an activity of the patient (e.g., values of states of the activity of the patient) and a state of the patient (e.g., values of states of the state of the patient). In an example, the state of the patient can include respective states indicating whether the patient is sitting, whether the patient is lying down, whether the patient is getting out of a bed, whether the patient is standing, whether the patient is walking, whether the patient is on a floor, more state values, fewer state values, or a combination thereof. In an example, the activity of the patient can include respective states indicating whether the patient eating, whether the patient is drinking, whether the patient is waving, more state values, fewer state values, or a combination thereof.

In an example, and as described with respect to FIG. 9, the technique 1100 can further include obtaining, from a third image of the image stream, third states of the part of the room of the patient; responsive to determining that the third states include a monitored condition, recording a time associated with the monitored condition; obtaining, from a fourth image of the image stream, fourth states of the part of the room of the patient; and, responsive to determining that the fourth states include the monitored condition and that the monitored condition persisted for a threshold duration of time, transmitting a second notification to the server. The second notification can include an indication of the monitored condition. In an example, the second notification can also include the threshold duration of time of the monitored condition.

In an example, and as described with respect to FIG. 9, the technique 1100 can further include obtaining, from a fifth image of the image stream, fifth states of the part of the room of the patient, where the fifth image is subsequent to the fourth image in the image stream; and, responsive to the fifth states not including the monitored condition, resetting the time associated with the monitored condition.

Another aspect of the disclosed implementations includes a system that includes a server, a user device, and a monitoring device. The monitoring device can be configured to obtain an image stream of at least a part of the room, where the image stream includes a first image and a second image that is subsequent to the first image in the image stream; identify first states based on the first image; identify second states based on the second image; compare the first states to the second states to identify a first active state; and, in response to identifying the first active state, transmit a first notification to the server. The first notification can include the second image. The server can be configured to, responsive to receiving the first notification, transmit the second image to the user device. As mentioned above, active states encompass active states and persistent states.

In an example, the first notification can include the first active state and the server can be further configured to transmit, to the user device, the first active state. The second image can be displayed with a highlight on the user device. In an example, the image stream further includes a third image and a fourth image. The monitoring device can be further configured to identify a second active state in the third image; record a time of identifying the second active state; and, responsive to identifying the second active state in the fourth image and the second active state persisting for at least a threshold duration of time, transmit a second notification to the server. The second notification can include an indication (e.g., a description) of the second active state.

In an example, the server can be further configured to receive, from the user device, a first request to display the image stream on the user device; transmit, to the monitoring device, a second request to transmit the image stream to the server; and transmit the image stream to the user device.

In an example, the image stream can further include a third image subsequent to the second. The monitoring device can be further configured to identify third states based on the third image; responsive to determining that the third states do not differ from the second states, not transmitting the third image to the server; and, responsive to determining that the third states differ from the second states, transmitting a second notification to the server, wherein the second notification comprises the third image.

Another aspect is an apparatus for monitoring a monitored environment. The apparatus includes a camera and a processor. The processor can be configured to obtain an image stream of at least a part of the monitored environment; apply image classification to a first image of the image stream to obtain first classification labels; apply the image classification to a second image of the image stream to obtain second classification labels; identify state differences by comparing the first classification labels to the second classification labels; and, responsive to identifying state differences, transmit the state differences to a server. The first classification labels and the second classification labels can each be obtained using a multi-label image classification model.

In an example, the processor can be further configured to set a monitored condition of the monitored environment based on the first classification labels; apply the image classification to a third image of the image stream to obtain third classification labels; and, responsive to the third classification labels including an indication of the monitored condition and the monitored condition persisting for a threshold duration of time, transmit a notification of the monitored condition. In an example, the monitored condition indicates whether a patient has not moved in at least the threshold duration of time. In an example, the monitored condition indicates whether the patient has not been detected in an image in at least the threshold duration of time.

As mentioned above with respect to FIGS. 4 and 9, an ML model (e.g., a multi-label classification model) can be used to infer the state of a monitored environment. In an example, the ML model can be a deep-learning convolutional neural network (CNN). In a CNN, a feature extraction portion typically includes a set of convolutional operations, which is typically a series of filters that are used to filter an input (e.g., an image) based on a filter (typically a square of size k, without loss of generality). For example, in machine vision (i.e., the processing of an image of a patient's room), these filters can be used to find features in an input image. The features can include, for example, edges, corners, endpoints, and so on. As the number of stacked convolutional operations increases, later convolutional operations can find higher-level features.

In the CNN, a classification portion is typically a set of fully connected layers. The fully connected layers can be thought of as looking at all the input features of an image in order to generate a high-level classifier. Several stages (e.g., a series) of high-level classifiers eventually generate the desired classification output. In a multi-label classification network, the number of outputs from the output layer can be equal to the number of desired classification labels. In an example, and as described above, each output can be a binary value indicating whether the state corresponding to the binary value is set or not set (e.g., on or off).

As mentioned, a typical CNN network is composed of a number of convolutional operations (e.g., the feature-extraction portion) followed by a number of fully connected layers. The number of operations of each type and their respective sizes is typically determined during a training phase of the machine learning. As a person skilled in the art recognizes, additional layers and/or operations can be included in each portion. For example, combinations of Pooling, MaxPooling, Dropout, Activation, Normalization, BatchNormalization, and other operations can be grouped with convolution operations (i.e., in the features-extraction portion) and/or the fully connected operation (i.e., in the classification portion). The fully connected layers may be referred to as Dense operations. As a person skilled in the art recognizes, a convolution operation can use a SeparableConvolution2D or Convolution2D operation.

A convolution layer can be a group of operations starting with a Convolution2D or SeparableConvolution2D operation followed by zero or more operations (e.g., Pooling, Dropout, Activation, Normalization, BatchNormalization, other operations, or a combination thereof), until another convolutional layer, a Dense operation, or the output of the CNN is reached. A convolution layer can use (e.g., create, construct, etc.) a convolution filter that is convolved with the layer input to produce an output (e.g., a tensor of outputs). A Dropout layer can be used to prevent overfitting by randomly setting a fraction of the input units to zero at each update during a training phase. A Dense layer can be a group of operations or layers starting with a Dense operation (i.e., a fully connected layer) followed by zero or more operations (e.g., Pooling, Dropout, Activation, Normalization, BatchNormalization, other operations, or a combination thereof) until another convolution layer, another Dense layer, or the output of the network is reached. The boundary between feature extraction based on convolutional networks and a feature classification using Dense operations can be marked by a Flatten operation, which flattens the multidimensional matrix from the feature extraction into a vector.

In a typical CNN, each of the convolution layers may consist of a set of filters. While a filter is applied to a subset of the input data at a time, the filter is applied across the full input, such as by sweeping over the input. The operations performed by this layer are typically linear/matrix multiplications. The activation function may be a linear function or non-linear function (e.g., a sigmoid function, an arcTan function, a tan H function, a ReLu function, or the like).

Each of the fully connected operations is a linear operation in which every input is connected to every output by a weight. As such, a fully connected layer with N number of inputs and M outputs can have a total of N×M weights. As mentioned above, a Dense operation may be generally followed by a non-linear activation function to generate an output of that layer.

An example of training the ML model is now described. In a first step, a respective number of images (e.g., 100, 1000, or any number of images) of every state that the ML model is to detect are collected. In a second step, each of the images is labeled (such as by a human) with the multiple labels that apply to the image. In a third step, a label list file that contains the image file names and associated labels is generated. In a fourth step, a certain percent of the image (e.g., 10% of the images, or some other percentage) is allocated for training validation of the ML model. A certain percent of the images can also be allocated to the training testing of the ML model. In a fifth step, the architecture of the ML model is defined. That is, a number of convolution layers, a number of fully connected layers, a size of the output layer, activation functions, and other parameters of the ML model are defined. It is noted that this step can be iterative until the ML model converges. In a sixth step, the training images are run through the defined model. In a seventh step, the trained model (e.g., the parameters and weights) is saved. The saved model can then be included in the monitoring device to perform, inter alia, the technique 900 of FIG. 4. In an example, the images may be pre-processed before being input to the ML model. In an example, the images may be resized. In an example, the images can be resized to a size of 300×300.

In an example, the ML model can include the following layers: flattening layers to reshape an input image into a format suitable for the convolutional layers and one or more fully connected layers; one or more convolutional layers; dense layers having respectively 128, 64, and 32 layers and using the Rectified Linear Unit (ReLu) function as an activation function; and a dense layer having 10 units and using the softmax function as an activation function.

The training process can be iterative and continuous. As more images and more patient room environments become available, the ML model can be retrained. Additionally, in order to optimize accuracy of the human pose detection, the training images used can be changed using respective hospital room images. That is, for each hospital or each set of similar hospital room set ups, a different trained model can be obtained. In an example, as part of an initial process of deploying a system according to implementations of this disclosure at a medical facility (e.g., a hospital), images of existing hospital rooms are taken and fed into the training set and the ML model is retrained. For example, hospitals may have certain bed models that require training the ML model to detect states.

For simplicity of explanation, the techniques 400, 500, 700, 900, and 1100 of FIGS. 4, 5, 7, 9, and 11, respectively, are depicted and described as a series of blocks, steps, or operations. However, the blocks, steps, or operations in accordance with this disclosure can occur in various orders and/or concurrently. Additionally, other steps or operations not presented and described herein may be used. Furthermore, not all illustrated steps or operations may be required to implement a technique in accordance with the disclosed subject matter.

The word "example" is used herein to mean serving as an example, instance, or illustration. Any aspect or design described herein as "example" is not necessarily to be construed as being preferred or advantageous over other aspects or designs. Rather, use of the word "example" is intended to present concepts in a concrete fashion. As used in this application, the term "or" is intended to mean an inclusive "or" rather than an exclusive "or." That is, unless specified otherwise or clearly indicated otherwise by the context, the statement "X includes A or B" is intended to mean any of the natural inclusive permutations thereof. That is, if X includes A; X includes B; or X includes both A and B, then "X includes A or B" is satisfied under any of the foregoing instances. In addition, the articles "a" and "an" as used in this application and the appended claims should generally be construed to mean "one or more," unless specified otherwise or clearly indicated by the context to be directed to a singular form. Moreover, use of the term "an implementation" or the term "one implementation" throughout this disclosure is not intended to mean the same implementation unless described as such.

Implementations of the monitoring device 300, and/or any of the components therein described with respect to FIG. 3 (and the techniques, algorithms, methods, instructions, etc., stored thereon and/or executed thereby) can be realized in hardware, software, or any combination thereof. The hardware can include, for example, computers, intellectual property (IP) cores, application-specific integrated circuits (ASICs), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

Further, in one aspect, for example, the monitoring device 300 can be implemented using a general purpose computer or general purpose processor with a computer program that, when executed, carries out any of the respective methods, algorithms, and/or instructions described herein. In addition, or alternatively, for example, a special purpose computer/processor can be utilized which can contain other hardware for carrying out any of the methods, algorithms, or instructions described herein.

Further, all or a portion of implementations of this disclosure can take the form of a computer program product accessible from, for example, a computer-usable or computer-readable medium. A computer-usable or computer-readable medium can be any device that can, for example, tangibly contain, store, communicate, or transport the program for use by or in connection with any processor. The medium can be, for example, an electronic, magnetic, optical, electromagnetic, or semiconductor device. Other suitable mediums are also available.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method, comprising:
obtaining, by a monitoring device, an image stream of at least a part of a room of a patient;
identifying, by the monitoring device from a first image of the image stream, first states of the part of the room;
identifying, by the monitoring device from a second image of the image stream, second states of the part of the room;
comparing, by the monitoring device, the first states to the second states to identify a change indicating an active state;
transmitting, by the monitoring device in response to identifying the active state, a notification to a server; and
transmitting, by the server in response to receiving the notification, an alert to a user device associated with a healthcare provider.

2. The method of claim 1, wherein the notification includes the second image.

3. The method of claim 1, further comprising displaying, on the user device, the second image along with details of the active state.

4. The method of claim 1, further comprising categorizing the active state into one of predefined health or safety concerns.

5. The method of claim 4, wherein the predefined health or safety concerns include potential fall risk, bed sore risk, or unattended patient movement.

6. The method of claim 1, further comprising applying a multi-label image classification model to obtain the first states and the second states.

7. The method of claim 1, wherein the active state is determined based on a difference in patient position.

8. The method of claim 1, wherein the active state is determined based on a difference in a condition of the room.

9. The method of claim 1, further comprising generating a summary report of active states identified during a monitoring period.

10. The method of claim 1, wherein the alert to the healthcare provider includes options to acknowledge the alert, request further information, or initiate a communication with the room.

11. A system for monitoring patient environments, comprising:
a monitoring device configured to:
obtain an image stream of at least a part of a room of a patient;
identify first states of the part of the room from a first image of the image stream;
identify second states of the part of the room from a second image of the image stream;
compare the first states to the second states to identify a change indicating an active state; and
transmit a notification in response to identifying the active state to a server;
the server configured to:
receive the notification from the monitoring device; and
transmit an alert in response to the notification to a user device; and
the user device associated with a healthcare provider configured to
receive the alert from the server.

12. The system of claim 11, wherein the notification includes the second image.

13. The system of claim 11, wherein the user device is further configured to display the second image along with details of the active state.

14. The system of claim 11, wherein the monitoring device is further configured to categorize the active state into one of predefined health or safety concerns.

15. The system of claim 14, wherein the predefined health or safety concerns include potential fall risk, bed sore risk, or unattended patient movement.

16. The system of claim 11, wherein the monitoring device is further configured to apply a multi-label image classification model to obtain the first states and the second states.

17. The system of claim 11, wherein the active state is determined based on one of a difference in patient position or a difference in a condition of the room.

18. Non-transitory computer-readable media having stored thereon instructions that, when executed by one or more processors, cause the one or more processors to perform operations comprising:
obtaining, by a monitoring device, an image stream of at least a part of a room of a patient;
identifying, by the monitoring device from a first image of the image stream, first states of the part of the room;
identifying, by the monitoring device from a second image of the image stream, second states of the part of the room;
comparing, by the monitoring device, the first states to the second states to identify a change indicating an active state;
transmitting, by the monitoring device in response to identifying the active state, a notification to a server; and
transmitting, by the server in response to receiving the notification, an alert to a user device associated with a healthcare provider.

19. The non-transitory computer-readable media of claim 18, wherein the operations further comprise displaying on the user device, the second image along with details of the active state.

20. The non-transitory computer-readable media of claim 18, wherein the operations further comprise categorizing the active state into one of predefined health or safety concerns.

* * * * *